United States Patent [19]

Tomita

[11] Patent Number: 4,822,568

[45] Date of Patent: Apr. 18, 1989

[54] APPARATUS FOR MEASURING AGGREGATION RATE OF WHOLE BLOOD RED BLOOD CELLS

[76] Inventor: Minoru Tomita, 26 Minaminakamachi, Motojukucho, Okazaki City, Aichi Prefecture, Japan

[21] Appl. No.: 874,558

[22] Filed: Jun. 16, 1986

[30] Foreign Application Priority Data

Mar. 28, 1986 [JP] Japan .............................. 61-070404

[51] Int. Cl.$^4$ ........................................... G01N 15/05
[52] U.S. Cl. ................................... 422/73; 128/691; 356/39; 422/110; 436/69; 436/70
[58] Field of Search ................... 422/73, 110; 436/69, 436/70; 356/39; 128/633, 637, 691

[56] References Cited

U.S. PATENT DOCUMENTS

| 3,463,614 | 8/1969 | Leslie . | |
| 4,398,894 | 8/1983 | Yamamoto | 422/73 X |
| 4,436,827 | 3/1984 | Tamagawa | 422/73 X |
| 4,576,477 | 3/1986 | Corbet et al. | 356/39 |

OTHER PUBLICATIONS

Benis et al., "Study of erythrocyte aggregation by blood viscometry at low shear rates," Circulation Research 22:29-41 1968.
Chien et al., 1966 "Effects of hematocrit and plasma proteins on human blood rheology at low shear rates" American Physiological Society 21:81-87.
Schmid-Schonbein et al., 1973 "Microrheology and protein chemistry of pathological red cell aggregation (blood sludge) studied in vitro" 10:213-227 Biorheology.
Brinkman et al., "Quantitative evaluation of the rate of rouleaux formation of erythrocytes by measuring light reflection (syllectometry)" in Proc. Kon. Ned. Akad. Wet., Ser. C (Biol. Med.) 66:236-248 1963.
Berman et al., "Quantitative red blood cell aggregometry of human and hamster bloods", Proc. VIIth Conference on Microcirculation (Aberdeen 1972) Karger. Basel 117-124 1973.
Usami et al., "Optical reflectometry of red blood cell aggregation under shear flow" Proc. VIIth Conference on Microcirculation (Aberdeen 1972), Karger, Basel, 91-98 1973.
Schmid-Schonbein et al., "A counter-rotating rheoscope chamber for the study of the microrheology of blood cell aggregation by micro-scopic observation and microphotometry" Microvascular Research 6:366-376 1973.
Shiga et al., "Kinetics of rouleaux formation using TV image analyzer. I. Human erythrocytes." American Physiological Society 245:H252-H258 1983.
Schmid-Schonbein et al., "New hemorheological techniques for the routine laboratory" in RACD vol. II Supplement 1981.

(List continued on next page.)

Primary Examiner—Barry S. Richman
Assistant Examiner—Jill Johnston
Attorney, Agent, or Firm—Edward D. C. Bartlett

[57] ABSTRACT

A whole blood aggregometer of red blood cells (RBC) consists of a transparent tube containing freshly drawn heparinized blood, and a densitometer head which is attached to the tube. The densitometer head consists of a light source and a light detector to monitor changes in optical density of the blood in the tube. The blood in the tube is first subjected to rapid flow with a solenoid, so that the wall shear rate of the blood approximates to 500 $s^{-1}$. The shear gives rise to a rapid increase in optical density of the blood due to dispersion of the blood corpuscles. The blood is then brought abruptly to a full stop. After the flow has stopped, the densitometer head reveals a gradual decrease in optical density in association with RBC aggregate formation. The resultant pattern is termed as an "RBC aggregogram". The RBC aggregogram exhibits a quasi-exponential decay in its initial part, which is followed by an asymptotical decrease. A mathematical procedure is employed to calculate the rate constant of the initial decrease from the two values on the RBC aggregogram at 10 s and 20 s. The rate constant $k_{10}$ is 0.192+0.028 for feline blood, and 0.129+0.012 for human blood. The RBC aggregation rate varies linearly with the hematocrit below 40%.

6 Claims, 23 Drawing Sheets

OTHER PUBLICATIONS aggregometer to the carotid artery, jugular vein, and femoral vein in cats" Proc. International Congress of Angiology, 1985.

Chien et al., "Blood viscosity: Influence of erythrocyte aggregation." Science 157:829–831, 1967.

Gustafsson et al., "Effects of increased plasma viscosity and red blood cell aggregation on blood viscosity in vivo." American Physiological Society 241:H513–H518 1981.

Klose et al., "Microrheology and light transmission of blood. I. The photometric effects of red blood cell aggregation and red cell orientation." Pflugers Arch. 333:126–139, 1972.

Tomita et al., "Photoelectric method for estimating hemodynamic changes in regional cerebral tissue." American Physiological Society 235:H56–H63, 1978.

Tomita et al., "Whole blood RBC aggregometer for human and feline blood." American Physiological Society 1986.

Zijlstra et al., "The Influence of Plasma Substitutes on the Suspension Stability of Human Blood" Proc. Kon. Ned. Akad. Wet., Ser. C. (Biological Medicine) 68:412–423 1965.

Wells et al., "Influence of fibrinogen on flow properties of erythrocyte suspensions." American Physiological Society 207: 1035–1040 1964.

Tomita et al., "RBC aggregometer applicable to transparent tubes containing blood and to in vivo vessels" Proc. Xth Inc. Congr. Angiol, 390 (Abstract) 1976.

Kobatake et al., "Red blood cell aggregation in occlusive cerebrovascular disease" Acta. Neurol. Scand. 60(Suppl. 72): 612–613 (Abstract) 1979.

Shinohara et al., "Hyperaggregability of red blood cells in patients with occlusive cerebrovascular disease". In Cerebral Vascular Disease 5 Excerpta Medica, Elsevier Science Publishers, 1985.

Saitoh et al., "Influence of RBC-aggregation on CBF in patients with occlusive CVD." Abstract, XVIIth International Congress of Internal Medicine 1984 Kyoto.

Jenkins et al., "Fundamentals of Optics" International Student Edition, Third Edition, Published by McGraw-Hill/Kogakusha, Ltd. Tokyo, pp. 455–458 1957.

Tomita et al., "Effects of hemolysis, hematocrit, RBC swelling, and flow rate on light scattering by blood in a 0.26 cm ID transparent tube" 1983 Biorheology 20:485–494.

Tomita, "Theory of inert gas method for measurement of cerebral blood flow and the assumptions underlying its background. II. Slug injection method" in Hiroshima J. Anesthesia 8: 127–137.

Schmid-Schonbein et al., "Microrheology and light transmission of blood. III. The velocity of red cell aggregate formation", 1975 Pflugers Arch. 354:299–317.

Jacobs et al. "A low shear tube viscometer for blood" 1969 Biorheology 6:121–126.

Tanahashi et al., "Application of whole blood RBC

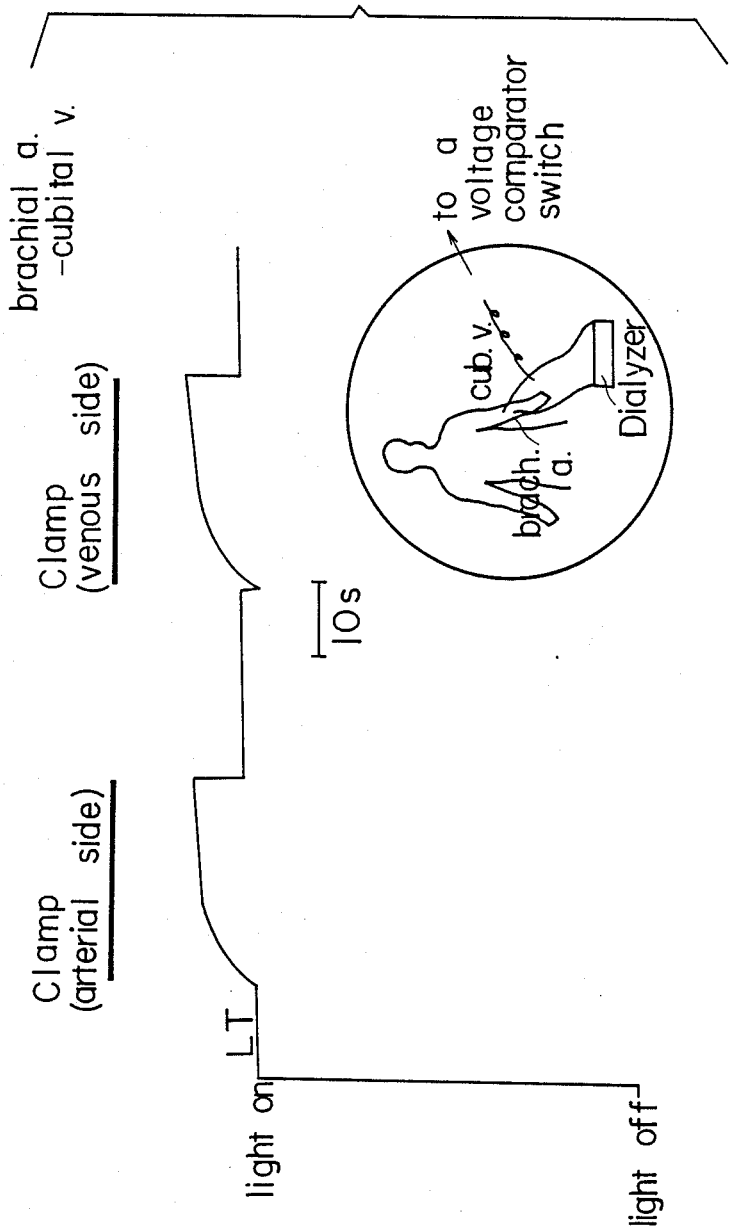

APPARATUS FOR MEASURING AGGREGATION RATE OF WHOLE BLOOD RED BLOOD CELLS

FIELD OF THE INVENTION

This invention relates to a method of measuring the aggregation rate of whole blood red blood cells and an apparatus used for such measurement.

BACKGROUND OF THE INVENTION

The aggregation rate of red blood cells (RBC) is known to increase in certain pathological conditions, and the aggregated cells presumably influence the microcirculation in the tissues of the body organs. To quantify the RBC aggregation rate, many techniques have been developed. Measurement of erythrocyte sedimentation rate (ESR) by Fahraeus was the first and is disclosed in a paper by him in 1921 entitled "Suspension-Stability of the Blood" in Acta Med. Scand. 55:1-228. However, it remains doubtful whether the ESR represents a suitable measure for this purpose.

Viscometry of whole blood at very low shear rates was the next technique and is disclosed in the following papers: Benis A. M., and J. Lacoste, 1968, "Study of erythrocyte aggregation by blood viscometry at low shear rates." Circ. Res. 22:29-41; Wells, R. E., Jr., T. H .Gawronski, P. M. Cox, and R. D. Perera, 1964, "Influence of fibrinogen on flow properties of erythrocyte suspensions." Amer. J. physiol. 207:1035-1040; and Chien, S., S. Usami, H. M. Taylor, J. L. Lundberg, and M. I. Gregersen, 1966, "Effect of hematocrit and plasma proteins on human blood rheology at low rates of shear." J. Appl. Physiol. 21:81-87. But this technique was criticized in a paper by H. Schmid-Schönbein, G. Gallasch, E. Volger, and H. J. Klose entitled "Microrheology and protein chemistry of pathological red cell aggregation (blood sludge) studied in vitro" in Biorheology, 1973, Volume 10, pages 213-227. They argued that the hydrodynamic effects of pathological RBC aggregates on the torque transmission through RBC suspensions constituted an insufficient system for rheological quantification of the RBC aggregation, and that the enhanced tendency to aggregation also prevented accurate measurement of the viscous effect in flow due to pronounced phase separation.

Quantitative evaluation of the rate of RBC aggregation (rouleaux formation) was successfully performed by Brinkman et al by measuring the light reflection ("syllectometry") of the blood—see a paper by Brinkman, R., W. G. Zijlstra, and N. J. Jansonius in 1963 entitled "Quantitative evaluation of the rate of rouleaux formation of erythrocytes by measuring light reflection ("syllectometry")" in Proc. Kon. Ned. Akad. Wet., Ser. C (Biol. Med.) 66:236-248. Subsequently, the principle of photometric aggregometry has been extended by several investigators as disclosed in the following papers: Berman, H. J., and R. I. Fuhro, 1973, "Quantitative red blood cell aggregometry of human and hamster bloods." Proc. VIIth Conference on Microcirculation (Aberdeen 1972) Karger, Basel, 117-125; Usami, S., and S. Chien, 1973, "Optical reflectometry of red blood cell aggregation under shear flow." Proc. VIIth Conf. on Micro-circulation (Aberdeen 1972) Karger, Basel, 91-98; Scmid-Schönbein, H., J. V. Gosen, L. Heinich, H. J. Klose, and E. Volger entitled "A counter-rotating "rheoscope chamber" for the study of the microrheology of blood cell aggregation by microscopic observation and microphotometry", 1973, Microvascular Research 6:366-376; and Shiga, T., K. Imaizumi, N. Harada, and M. Sekiya, 1983, "Kinectics of rouleaux formation using TV image analyzer." I Human erythrocytes, Amer. J. Physiol. 245:H252-H258. However, these techniques are rather complicated for common use.

Recently Schmid-Schönbein et al constructed an automatic red cell aggregometer, improving their "rheoscope", which permits transmission photometry of RBC aggregate formation after shearing the blood in a counter-rotating cone chamber - see a paper by Schmid-Schönbein, H., E. Volger, P. Teitel, H. Kiesewetter, U. Dauer, and L. Heilmann entitled "New hemorheological techniques for the routine laboratory" in RACD Vol. II Supplement 1981. However, such aggregometer is expensive and has problems in that asymptotical baseline is unstable.

SUMMARY OF THE INVENTION

The present invention is concerned with solving or mitigating the above-described problems or disadvantages by providing a method of measuring the aggregation rate of red blood cells (RBC) and an apparatus (aggregometer) therefor which are different in both principle and methodologically from the prior art, which can be made comparatively cheaply, are easy to use, and result in the advantage of being easily operated by nurses at a bedside.

Another object of the invention is to provide an aggregometer which not only can be used for measuring the aggregation rate of blood from a patient, but can also be applied to blood vessels in situ, and for monitoring of circulation in conjunction with renal dialysis and artificial cardio-pulmonary apparatus.

Accordingly, therefore, there is provided by the present invention a method for measuring aggregation rate of whole blood red blood cells wherein light is illuminated from one side of a tube, and changes of optical density of the light transmitted through the blood caused by changes of flow rates of said blood are detected to determine the rate of aggregation of said blood.

The optical density may be measured when the whole blood in the tube is caused to change from a flow state to rest state.

The tube may comprise an artery or a vein, and the rate of aggregation of the whole blood be determined by measuring the optical density of light transmitted through the artery or the vein. The change in the flow rate of the blood may be caused by blocking or releasing the blocking of the artery or the vein at an upstream location or a downstream location.

The tube may comprise a blood circulatory tube in renal dialysis or artificial cardio-pulmonary apparatus.

According to another aspect of the present invention, there if provided an apparatus for measuring the aggregation rate of whole blood red blood cells, comprising a light source which emits light at one side of a tube through which the blood is caused to flow at a varying rate of flow, a densitometer head having a light detector which monitors light that has passed through the blood in the tube from the light source, and a recorder which records detection signals from the light detector.

The tube may advantageously be a cubital vein in an extracorporeal circulatory system. The densitometer may be connected to a voltage comparator switch of a warning device.

The extracorporeal circulatory system may advantageously be a renal dialysis or an artificial cardio-pulmonary apparatus.

Other objects, features and advantages of the present invention will become more fully apparent from the following detailed description of the preferred embodiment, the appended claims and the accompanying drawings.

BRIEF DESCRIPTION OF THE DRAWINGS

FIG. 28 is a diagram of a record demonstrating the practical applicability of the RBC aggregometer head as a warning device for flow disturbance in an extracorporeal circulatory system for blood dialysis in a patient with renal failure.

DETAILED DESCRIPTION OF THE PREFERRED EMBODIMENTS

Figure 1:
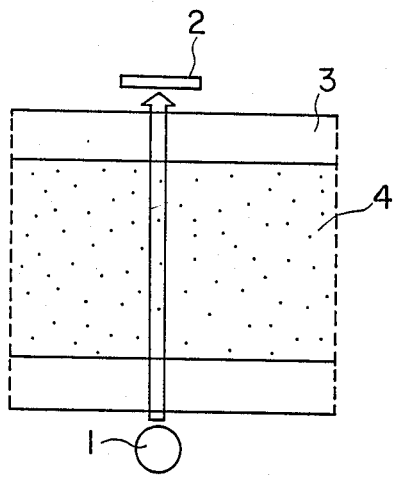
FIG. 1 is a diagram illustrating the method and apparatus of measuring the aggregation rate of RBC according to the present invention.

The principle of the invention will first be explained referring to Fig. 1. In a method of the invention, light is illuminated to whole blood 4 in a tube 3 from the side of the tube 3, and changes of optical density of light that has been transmitted through blood 4 in tube 3 are measured by varying the flow rate of whole blood 4 to determine the rate of aggregation of said blood.

An apparatus according to the invention comprises a light source 1 which illuminates light from the side of tube 3 to blood 4 of which velocity is varied in tube 3, a light receiving part 2 which receives light from light source 1 that has passed through blood 4 in tube 3 and a recorder that records detection signals from the light receiving part 2.

Various shear rates are imparted to blood 4 in the tube 3. Due to this shearing, aggregated red blood cells are caused to disaggregate and disperse, resulting in marked increase of optical density of light passing through blood 4. When this shearing is removed, blood 4 stops immediately bringing about aggregation of blood. Change of optical density at this stage is gradual and transmission of light in blood is slowly resumed. The whole blood RBC aggregation rate is determined by measuring this change of optical density.

METHOD

PRELIMINARY EXPERIMENT TO VISUALIZE THE FLOW EFFECT

A preliminary experiment was carried out in a dark room to visualize the flow effect induced by flow-dependent RBC aggregation and disaggregation. I prepared a 20 ml syringe containing heparinized whole blood freshly drawn from a healthy 22 year old girl, a transparent vinyl tube obtained from a dripping set used clinically for fluid infusion, and a stand. The blood was introduced into the vinyl tube, to which the syringe was connected, and flow was imparted by adjusting the height of the reservoir syringe. The flow rate was monitored with a photoelectric drip counter attached to the distal end of the tube. The flow was subjected to a full stop by clamping the vinyl tube with a surgical clamp. The vinyl tube was passed through a black celluloid pencil box, where the middle of the vinyl tube was spotlighted to transilluminate the blood from behind with a glass fiber of 0.1 cm OD. The light was supplied by a Xenon Lamp (Cold Light Supply, Olympus CLE-3, Olympus Optical Co., Tokyo). A photograph of the blood in the resting state transilluminated from behind was taken. The blood was then allowed to flow by releasing the clamp. Immediately after the resumption of blood movement, a second photograph of the blood was taken in the flowing state.

LIGHT SOURCE AND LIGHT DETECTOR OF THE DENSITOMETER HEAD

Figure 3:
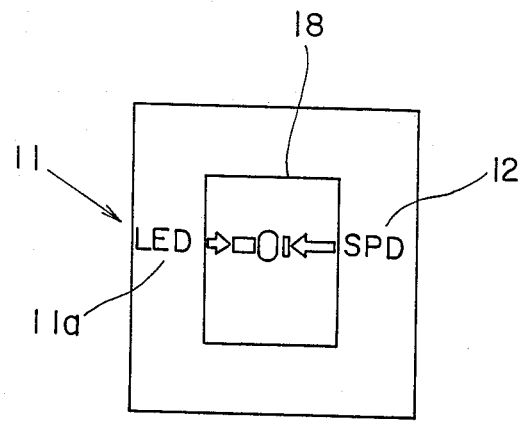
FIGS. 3 and 4 are diagrams of mechanical parts of the whole blood RBC aggregometer, FIG. 3 being a front view of densitometer head and FIG. 4 a side view of the aggregometer.
Figure 5:
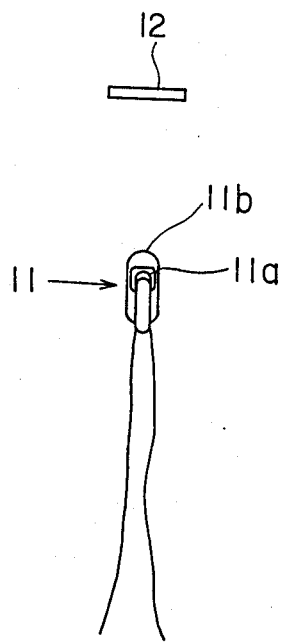
FIG. 5 is a view of light emitting diode (LED) at bottom sealed in a glass tube with a converging lens at the top end and a piece of bar element of silicon photodiode (SPD) at top.

In a light source 11, a light emitting diode (LED) 11a of gallium arsenide (Hamai Electric Co., Tokyo) which emitted infrared light of 950 nm in wavelength was used as the light source of the RBC aggregometer (FIG. 3). The reason to employ an infrared beam instead of visible light was as follows. Rayleigh's law for the dependence of scattering on wavelength predicted that the intensity of light transmitted through blood would be proportional to the fourth power of wavelength (see "Fundamentals of Optics" Third Edition, Internal Student Edition, 1957 by F. A. Jenkins and H. E. White, editors, McGraw-Hill/Kogakusha, Tokyo, pages 455–458): the transmission would thus be almost $(950/600)^4$ or 6 times greater than with the visible light employed above. Since the absorption of light by hemoglobin was minimum at this wavelength, the effect of oxygenation of the blood would be negligible. The Hamai product was made so that the LED was sealed in a miniature glass bulb of 0.12 cm OD and 0.3 cm in length which formed a converging lens 11b at the top end (FIG. 5). This lens converged the emitted invisible light into a narrow beam. Such was the narrow beam incident of the vinyl tube 13 that no aberrant light was directed towards the circumferential periphery of the tube. This is an essential prerequisite for RBC aggregometry by the present technique (see a paper by Tomita, M., F. Gotoh, M. Yamamoto, N. Tanahashi, and M. Kobari entitled "Effects of hemolysis, hematocrit, RBC swelling, and flow rate on light scattering by blood in a 0.26 cm ID transparent tube" in 1983 Biorrheology 20: 485–494), although there is some unavoidable biased light through the wall of the transparent vinyl tube.

Figure 4:
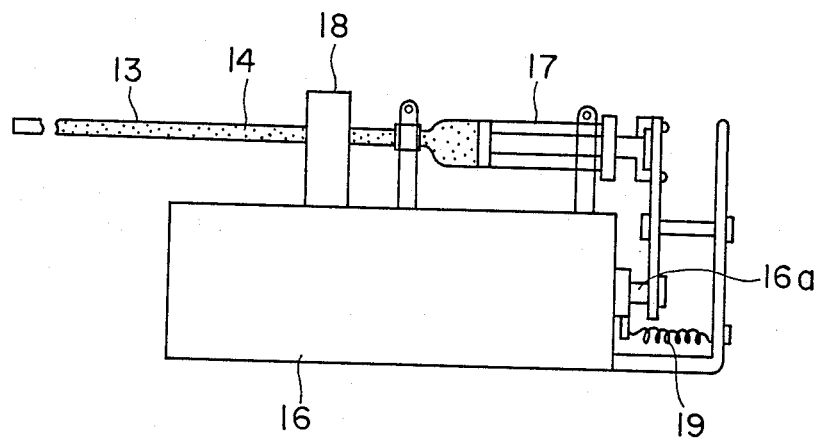

A silicon photodiode (SPD-550, Sharp Electric Co., Tokyo), a kind of solar battery, was used as the light detector. As shown in FIG. 4 (top), it consisted of a small bar element 12 of 0.2×0.5 cm² in sensitive surface area and 0.05 cm in thickness. With a parallel resistance of 5k ohms, it generated 0.20 V when facing the LED bulb at a separation of 1 cm with no interspaced material. The output of the SPD 12 was fed to a DC recorder 15 having a sensitivity equivalent to full scale per 10 mV (Rikadenki, Tokyo) for continuous recording of an "RBC aggregogram". The usual paper speed used was 15 cm/min.

DENSITOMETER HEAD

The advances in electronic technology of the LED and SPD described above, have made it feasible to construct a compact, light (1.0–3.0 g) and yet quite powerful densitometer head. The densitometer head was built out of a black polystyrene material as shown in FIG. 3, and the LED bulb and SPD were arranged facing each other as the point light source and point light detector, interspaced by a transparent vinyl tube of 0.26 cm ID, 0.40 cm OD and 30 cm in length. I also produced an adjustable type of densitometer head for the RBC aggregometer which could be applied to different sizes of vinyl tube or even vessels in situ narrower than 0.6 cm OD.

WHOLE BLOOD RBC AGGREGOMETER a. ASSEMBLY

The assembly consists of a mechanical part and an electronic part. As shown in FIG. 4, the plunger of the solenoid 16 (MD-211, Maruha Electric Co., Tokyo) was connected to the piston of a 1 ml plastic syringe 17, containing a heparinized blood sample from the subject to be studied. The syringe 17 was set in place connected to the vinyl tube 13, so that the initial part of the tube was filled with blood. The tube passed through the densitometer head just near the syringe 17 for monitoring changes in optical density of the blood (FIG. 4). The syringe 17 and tube 13 were placed in a chamber with the temperature adjusted to 37° C.

Figure 6:
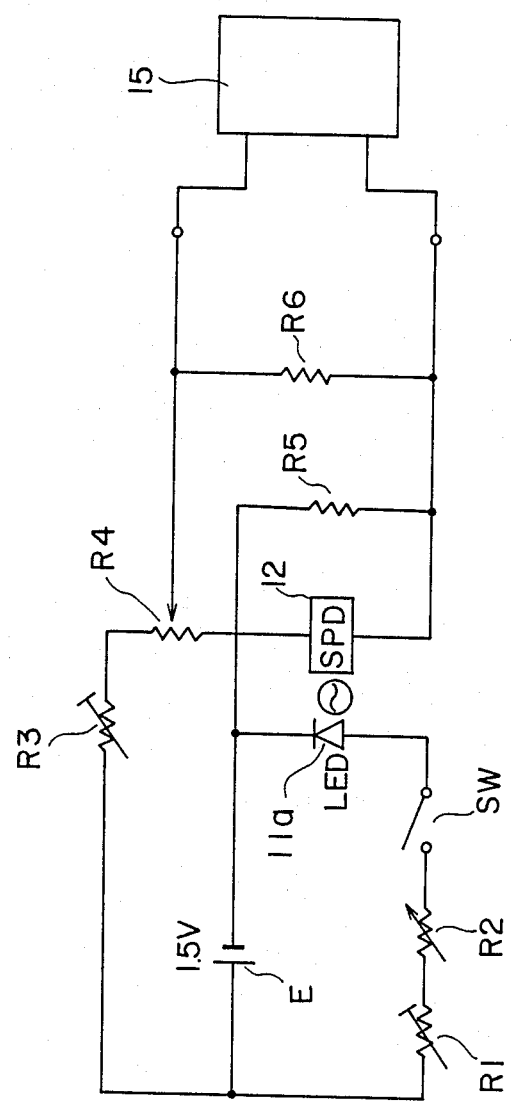
FIGS. 6 and 7 are respectively circuit diagrams of the recording and driving components of electronic parts of the whole blood RBC aggregometer of the invention.
Figure 7:
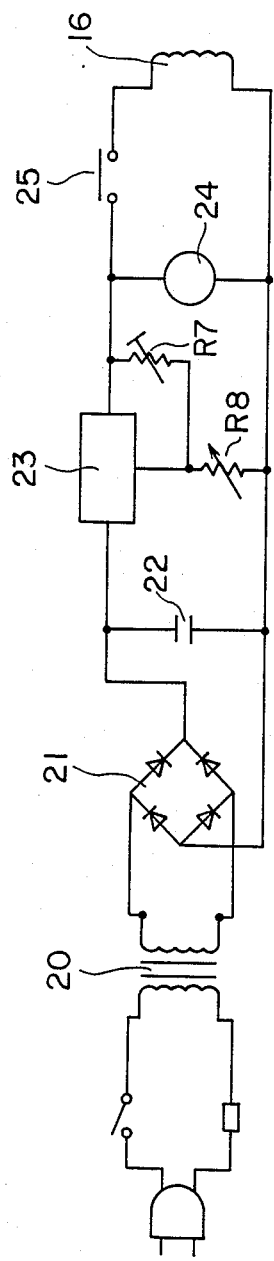

The electronic part is shown diagrammatically in FIGS. 6 and 7. The 30 V output of the A.C. transformer 20 was rectified biphasically and smoothed with a 4700 microfarad condenser 22. The resultant DC power controlled with a voltage regulator 23 at from 2.0 to 30.0 V was supplied to the solenoid 16 in order to push the syringe 17. A voltage was applied so that the blood flowed at a wall shear rate of ca. $500^{-1}$ as calculated simply from the velocity of the blood and the dimensions of the tube. The optical density of the blood was recorded continuously during the forward movement and full stop of the blood. The record was termed a "forward" RBC aggregogram. After a certain period (one or two minutes), the solenoid automatically returned to the previous state with a powerful wire spring 19, retracting the piston of the syringe and therefore causing backward movement of the blood. The corresponding record was termed a "backward" RBC aggregogram. The syringe 17 and tube 13 were disposable.

b. ANALYSIS OF RBC AGGREGOGRAM AND NORMAL RBC AGGREGATION RATE

As a quantitative measure of the rate of RBC aggregation (rouleaux formation), Brinkman et al (see previously mentioned paper by Brinkman, Zijlstra and Jansonius) used the half time ($T_{\frac{1}{2}}$) of the syllectogram (record of light reflection). However, their method for calculating the half time was rather complicated. Their estimation was made from four values of the syllectogram: the initial height obtained by extrapolation of the descending part of the syllectogram to time zero, and the heights corresponding to times 15, 30, and 45's. In addition to the number of sample values required, the half time so obtained was subject to error due to baseline instability. Schmid-Schönbein et al (see previously mentioned paper by Schmid-Schönbein, Volger, Teitel, Kiesewetter, Dauer and Heilmann) adopted the product of a rate constant multiplied by the plasma viscosity of the same blood as the "corrected aggregation constant". They computed the rate constant of the rapidly changing decay of the syllectogram from the area formed between the initial level and the syllectogram up to 10 s assuming that the fast component of the syllectogram was completed within the time. However, their analytical technique could not be applied to my RBC aggregogram since calibration of the area by initial deflection was difficult due to asymptotical baseline shift as illustrate in FIG. 8.

Figure 8:
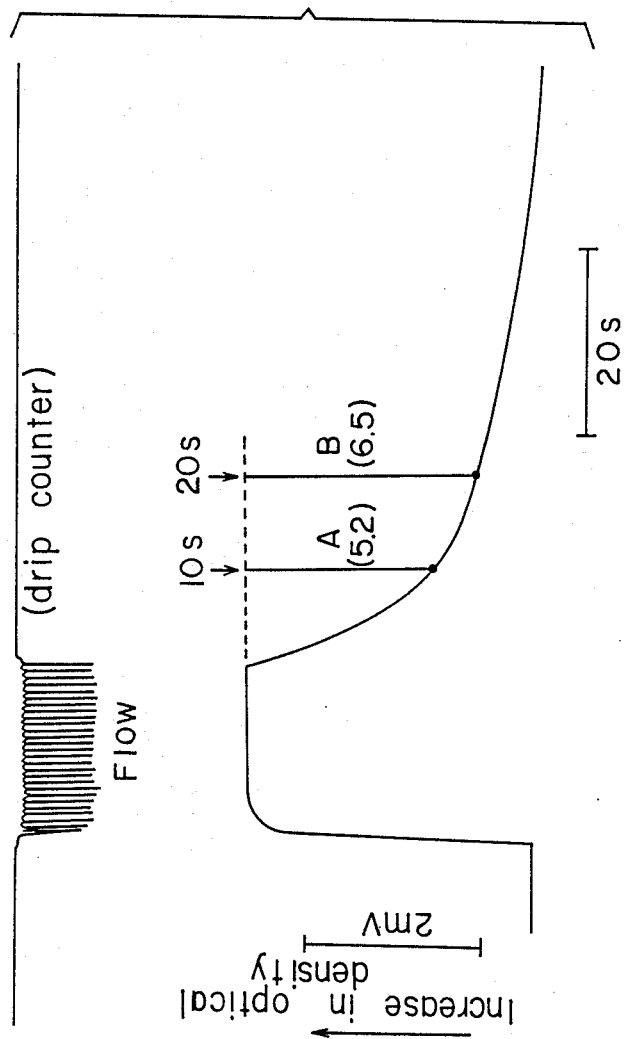
FIG. 8 is a diagram showing actual protocol of an RBC aggregogram of human whole blood, the shear of the blood is given by the height of the reservoir of blood, and the flow rate is indicated by the drip count.

This FIGURE shows an RBC aggregogram obtained with the densitometer head attached to the vinyl tube used for the above preliminary experiment. A constant flow was applied by controlling the height of the syringe. The flow rate recorded with a drip counter is shown in the top trace. The blood flow was then abruptly stopped by clamping the tube with a surgical clamp. Similar to the syllectogram reported by Brinkman et al (see previously mentioned paper by Brinkman, Zijlstra and Jansonius) and Schmid-Schönbein et al (see previously mentioned paper by Schmid-Schöbein, Teitel, Kieswetter, Dauer and Heilmann), the RBC aggregogram exhibited a quasi-exponential decay following stop of flow. However, it should be noted that there was no initial upstroke at the beginning of the aggregogram, of the type observed on the syllectogram of Brinkman et al (supra), and Schmid-Schönbein et al (supra). The upstroke was attributed by them to changes in the alignment and orientation of flowing red blood cells. The lack of initial upstroke on my RBC aggregogram was advantageous for making the analytical procedure simpler. The most common procedure for finding the time constant or the rate constant (reciprocal of time constant) of an exponential curve is from the iterative curve fitting a straight line on semilogarithmic paper, which is time consuming. To overcome this difficulty, I adopted a simple method for calculating the total deflection C and the rate constant k of the RBC aggregogram, assuming that it is a monoexponential curve $C(1-e^{-kt})$. This method was reported originally by me in my 1972 paper entitled "Theory of inert gas method for measurement of cerebral blood flow and the assumptions underlying its background. II. Slug injection method" in Hiroshima J. Anesthesia 8: 127-137. Firstly, a line parallel to the x axis was drawn at the origin of the RBC aggregogram as shown in FIG. 8. Two points on the RBC aggregogram corresponding to times T and 2T (A and B, respectively) were then read off. Although the choice of time 2T was arbitrary, I used 10 s as T and 20 s as 2T. The values of C and k were calculated according to the following equations:

$$C = A^2/(2A-B) \quad \quad \quad \quad 1$$

$$k = -(1/T)ln((B-A)/A) \quad \quad \quad \quad 2$$

The baseline level (C) and the rate constant (k) of exponential decay, of which only the initial part was recorded, can be calculated from the two heights, A at time T and B at time 2T, on the curve as follows:

$$A = C(1-e^{-kT})$$

$$B = C(1-e^{-2kT})$$

Taking the logarithm after rearrangement, $$-kt = ln(1-A/C)$$

$$-2kT = ln(1-B/C)$$

Eliminating kT, $$2ln(1-A/C) = ln(1-B/C)$$

$$(1-A/C)^2 = (1-B/C)$$

Solving for C, we have $$C = A^2/(2A-B)$$

Introducing values of $C_{10}$ and $A_{10}$ at T=10, $$A = C(1-e^{-10k_{10}})$$

Solving for k, we have $$k_{10} = -(1/10)ln(1-(2A-B)/A) = -(1/10)ln(-B-A)/A)$$

This method may be applied to any incomplete curve in which only part of the exponential curve is recorded. The value of k can be readily converted to the half time $(T_{\frac{1}{2}})$ as $T_{\frac{1}{2}} = 0.693/k$.

To examine the variability of k as a function of T, the descending part of the human RBC aggregogram in FIG. 8 was sampled at equally spaced times of every 1 s up to 20 s. The serial pairs in the deflection of $A_N$ at N s and $B_N$ at 2N s, i.e.. $A_1$ at 1 s and $B_1$ at 2 s, $A_2$ at 2 s and $B_2$ at 4 s, $A_3$ at 3 s and $B_3$ at 6 s,. . . , were used to calculate the corresponding values of k according to equation 2. The value of $k_{10}$ calculated from $A_{10}$ at 10 s and $B_{10}$ at 20 s was chosen as the representative rate constant of RBC aggregation of the blood under study. The corresponding level of the baseline $C_{10}$ was also calculated. The samples at every second in the deflection up to 20 s were then subtracted from $C_{10}$ and plotted on semilogarithmic paper against time. In this way, any deviation from the theoretical curve $y = C_{10}(1-e^{-k_{10}T})$ would become apparent. The linear regression line of the samples on the semilogarithmic paper by the method of least squares was calculated. The slope of the regression line was then compared with $k_{10}$. Similar analysis was carried out on 11 blood samples from 6 unstrained cats and 5 human subjects who had suffered no known physical disorders. The data was analyzed statistically by Student's t-test.

c. VARIATION OF RBC AGGREGATION RATE WITH HEMATOCRIT

In this series of experiments, 3 ml of heparinized blood was obtained from 26 cats which were subjected to several experimental procedures including hemodilution. To avoid individual preferences, one sample was used from each cat. All blood samples were tested for their RBC aggregation rate ($k_{10}$) using the whole blood RBC aggregometer described above. The blood samples were also analyzed for hematocrit (Hct), counts of red blood cells, white cells, and platelets, viscosity of the blood, and plasma proteins including the fibrinogen level. The RBC aggregation rate was correlated with Hct.

RESULTS

VISUALIZATION OF THE FLOW EFFECT

Figure 2:
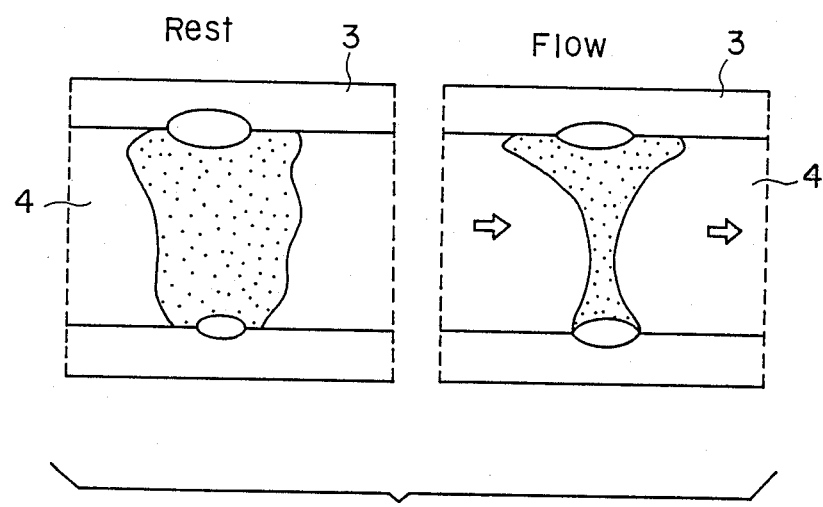
FIG. 2 is a diagram which shows changes in light transmission by blood at rest and flow states respectively.

FIG. 2 reproduces photographs (taken from above) of freshly drawn heparinized human whole blood in a vinyl tube in the resting state (left) and flowing state (right). The wall of the vinyl tube is shown schematically for the purposes of orientation. The arrows indicate the direction of flow. As shown in the FIGURE, the white light was filtered by the blood, and only transmitted red light was visible. When the blood was subjected to flow, the red rectangular image of the resting blood was transformed immediately to a coarctate shape. This enigmatical phenomenon occurring through the same mass of blood, can be explained by changes in spatial light scattering by the blood in association with flow-dependent RBC aggregation and disaggregation. In a previous series of experiments, I observed that the incident light became more scattered sidewards than transmitted by blood with flow, when the light intensity detected from the circumferential surface of the blood was plotted on polar coordinates (see previously mentioned paper by Tomita, Gotoh, Yamamoto, Tanahashi and Kobari). It was expected that the flow effect could be readily recorded when a small sensor as shown in FIG. 5 was placed at the center of the image in order to follow the chronological changes in apparent optical density of the blood.

RBC AGGREGOGRAM AND ITS REPRODUCIBILITY

Figure 9:
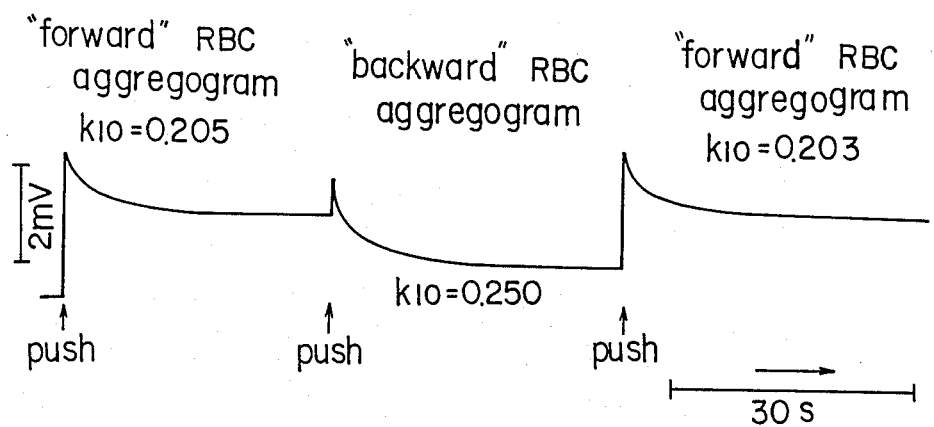
FIG. 9 is a diagram which shows continuous recording of forward RBC aggregogram with push of the blood, backward RBC aggregogram with pull of the blood and then forward RBC aggregogram with another push.

A continuous recording of "forward", "backward", and "forward" feline RBC aggregograms in succession is shown in FIG. 9. With flow of the blood by rapid pushing with the solenoid, the optical density of the blood increased greatly as demonstrated by a rapid upward deflection. Sudden stop of the flow initiated an immediate decrease in optical density in a quasi-exponential fashion, which was followed by a slow monotonous decrease. There was no definite sign in the RBC aggregogram indicating completion of rouleaux formation. As suggested by Brinkman et al. (supra), secondary factors appeared to cause a slight decrease after rouleaux formation was finished. Due to the ambiguous baseline level, I considered that the level of $C_{10}$ calculated above belonged to completed rouleaux formation. To repeat the measurement, push and pull of a blood sample were carried out alternately. It was quite peculiar to note that the backward RBC aggregogram in response to the pull procedure was different from the forward RBC aggregogram in its initial height, rate of decay and level of the baseline. The magnitude of the difference appeared to be variable in individual cases, but the changes were all identical in direction. The two different baselines upon push and pull were observed even with a non-aggregating blood suspension of 1% albumin solution.

Figure 10:
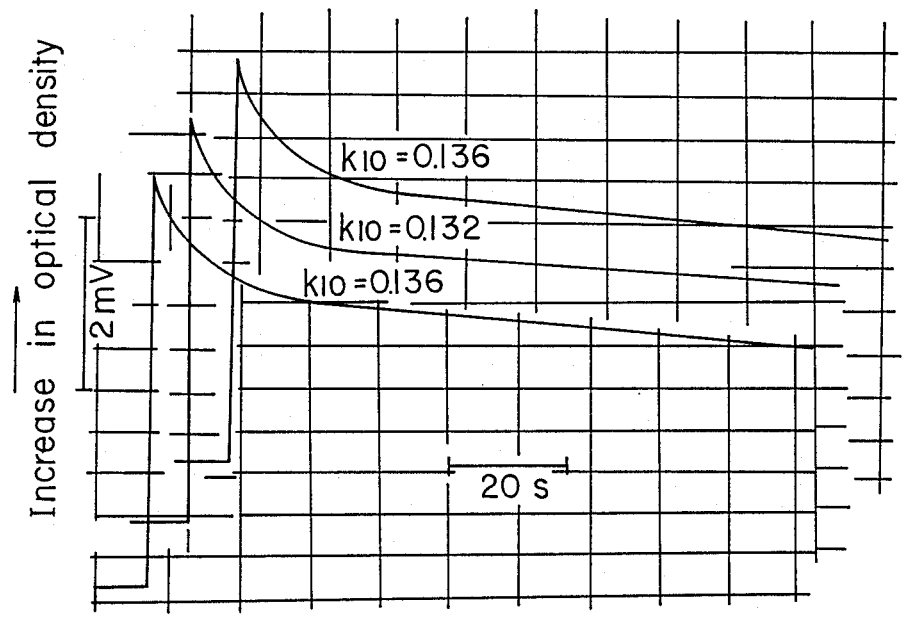
FIG. 10 is a diagram illustrating reproducibility of repeated forward RBC aggregograms for the same human whole blood.

When forward RBC aggregograms obtained consecutively with the same blood sample were compared, a good reproducibility was observed with respect to initial height, mode of decrease and baseline as shown in FIG. 10. The values of $k_{10}$ were 0.136, 0.132 and 0.136, respectively. The term "RBC aggregogram" refers hereafter to the forward RBC aggregogram, unless otherwise stated.

VARIATION OF k AND DEVIATION FROM EXPONENTIAL FUNCTION

Figure 11:
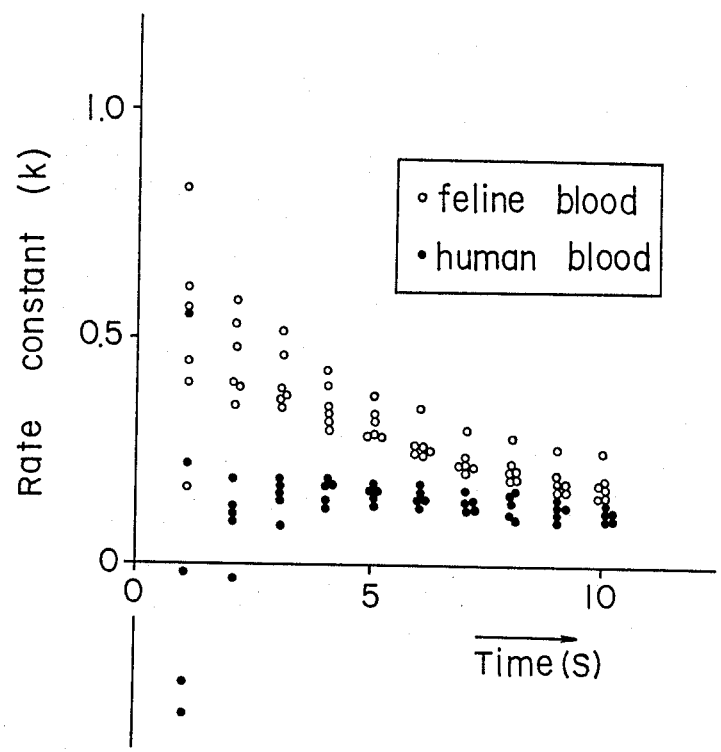
FIG. 11 is a diagram showing the change of constant k with time s, open and closed circles being feline and human RBC aggregograms respectively.

FIG. 11 shows values of k plotted against time t. The open circles were calculated from feline RBC aggregograms and the closed circles from human aggregograms. Clearly, k was not constant for both the feline and human RBC aggregograms, indicating that the decreases were not monoexponential. There was also a species difference: the value of k for feline blood was maximum at the beginning and decreased with time, whereas that of human blood tended to start with a low value and then formed a plateau. Despite this variability of k with time, the RBC aggregation rate could be compared according to the value of $k_{10}$, when the time was specified (e.g., 10 s for A and 20 S for B).

Figure 12:
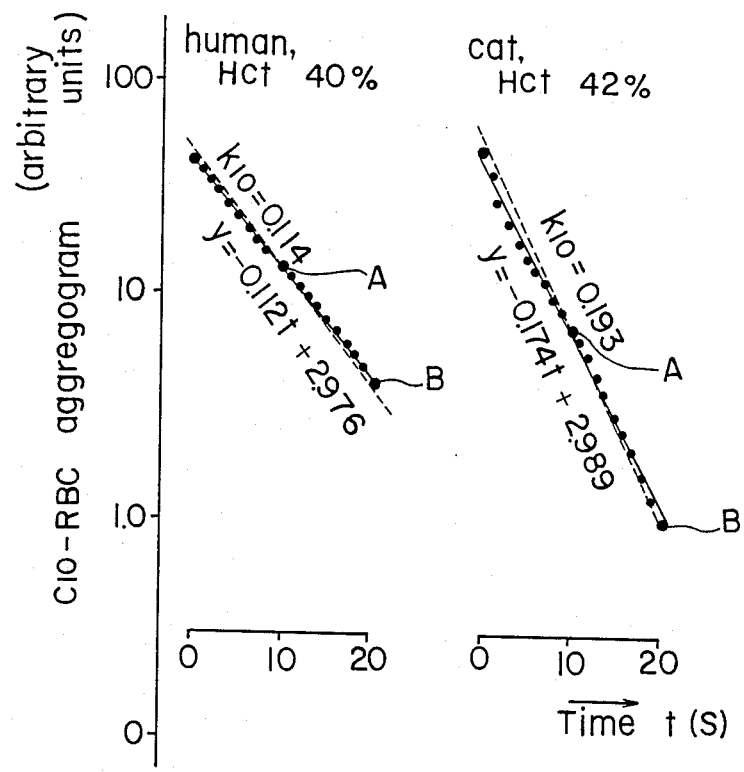
FIG. 12 is a diagram showing deviations of practical human and feline RBC aggregograms from the theoretical curves defined by $C_{10}$, the left and right graphs referring to human and feline blood respectively.

The deviations of actual RBC aggregograms from the theoretical curves defined by $k_{10}$ are shown in FIG. 12. The left graph from human blood follows a more or less even straight line whereas the right graph from feline blood exhibits a slight S-shape. The slope of the 5 human regression lines was ±0.012 (mean±SD) and the value of $K_{10}$ was 0.129±0.012. The correlation coefficient (r) between the slope and $k_{10}$ was 0.992(p<0.01). Similarly, the slope of the 6 feline regression lines was 0.170±0.025 and the value of $k_{10}$ was 0.192±0.028. The correlation coefficient (r) was 0.995(p<0.01). The values of $K_{10}$ for the human and feline blood were statistically significantly different (p<0.01).

Hct AND RBC AGGREGATION RATE

Table 1 below summarizes data for Hct, the value of $k_{10}$, the half time calculated from the relationship $T_{\frac{1}{2}}=0.693/k_{10}$, and fibrinogen level in twenty-six feline blood samples. It can be seen that the value of $k_{10}$ increased with Hct, but the increase of $k_{10}$ leveled off above an Hct of 40%. The regression line between Hct below 40% and $k_{10}$ was:

$$k_{10}=(5.51 \text{ Hct}-18)\times 10^{-3} \ (r=0.943, \ p<0.001).$$

In Table 1, $k_{10}$ represents RBC aggregation rate, and based on $k_{10}$, the aggregation rate may be expressed in terms of half time or $1/k_{10}$ (time constant).

TABLE 1

Hematocrit vs. RBC-aggregation

| Hct (%) | $k_{10}$ | Half time (s) |
|---|---|---|
| 15.0 | 0.073 | 9.49 |
| 20.0 | 0.102 | 6.79 |
| 27.0 | 0.119 | 5.80 |
| 28.0 | 0.133 | 5.20 |
| 29.0 | 0.140 | 4.95 |
| 29.0 | 0.140 | 4.95 |
| 32.0 | 0.146 | 4.75 |
| 32.0 | 0.137 | 5.05 |
| 34.5 | 0.162 | 4.27 |
| 35.0 | 0.160 | 4.33 |
| 35.0 | 0.170 | 4.01 |
| 35.5 | 0.174 | 3.98 |
| 36.0 | 0.212 | 3.26 |
| 38.0 | 0.187 | 3.70 |
| 39.0 | 0.206 | 3.36 |
| 39.0 | 0.207 | 3.35 |
| 39.0 | 0.216 | 3.21 |
| 40.0 | 0.190 | 3.60 |
| 42.0 | 0.208 | 3.33 |
| 44.0 | 0.214 | 3.20 |
| 44.0 | 0.219 | 3.16 |
| 54.0 | 0.224 | 3.00 |
| 55.0 | 0.237 | 2.90 |
| 56.8 | 0.226 | 3.00 | feline whole blood. $T_{\frac{1}{2}}$ = half time

The photometric changes of blood occurring in a tube during flow and stop are a reflection of the kinetics of red cell aggregate formation. In papers by Schmid-Schönbein, H., J. V. Gosen, L. Heinich, H. J. Klose, and E. Volger entitled "A counter-rotating "rheoscope chamber" for the study of the microrheology of blood cell aggregation by micro-scopic observation and microphotometry", 1973 Microvascular Research 6:366–376, and by Schmid-Schönbein, H., K. A. Kline, L. Heinich, E. Volger, and T. Fischer entitled "Microrheology and light transmission of blood. III. The velocity of red cell aggregate formation", 1975 Pflügers Arch. 354:299-317, they directly observed the red cell changes with their rheoscope and found that the cells were deformed and aligned in flow, randomly oriented at the moment of full stop of motion, and then began to form aggregates. The role of RBC aggregation in the changes in light transmission of whole blood within a tube was confirmed by previous experiments (see a paper by Tomita, M., F. Gotoh, T. Sato, M. Yamamoto, T. Amano, and N. Tanahashi entitled "RBC aggregometer applicable to transparent tubes containing blood and to in vivo vessels", 1976 Proc. Xth Inc. Congr. Angiol. 390. (Abstr.)) in which the typical photometric changes of blood disappeared when red cells were suspended in albumin solution or were hardened by glutaraldehyde treatment. In the albumin solution, the cells were able to deform and align to the flow stream, but not to aggregate being deprived of "bridging" proteins like fibrinogen or $\alpha_2$ globulin. The hardened cells were able to orient, but neither to deform nor to aggregate. The major photometric changes were concluded to be exclusively connected to RBC aggregation.

One prominent difference between the RBC aggregogram reported here and the syllectogram reported by Brinkman et al (supra) and Schmid-Schönbein, Volger, Teitel, Kiesewetter, Dauer and Heilmann (supra) is that our RBC aggregogram lacks an initial upstroke before the quasiexponential decay upon stop of flow (see FIG. 8). This phenomenon was explained on the basis that upon sudden stop of viscometric flow, the cells lose their orientation, assume their familiar resting biconcave shape and become irregularly oriented in space. Subsequently, typical rouleaux are formed with time. In the experiment with the suspension of RBC in albumin solution, I observed only a negligible increase in optical density of the suspension with stop of flow. The effect of orientation and alignment of red blood cells would thus be negligibly small in blood flow in a wide tube. The shear given would be sufficiently large to disaggregate and disperse red cells. However, the majority of flowing red cells would remain undeformed and only the red cells in the peripheral part would align along the wall. Further investigations are needed to elucidate the red cell behavior of flowing blood in large vessels.

Another point to note is the difference in baseline level between the forward RBC aggregogram and backward RBC aggregogram. I assume that the viscoelastic properties of whole blood might be involved with a positive pressure due presumably to the meniscus effect (see a paper by Jacobs, H. R. entitled "A low shear tube viscometer for blood" 1969 Biorheology 6:121-126 when the blood was pushed to cause flow in the tube, and with a negative pressure when pulled. The slight pressure difference might result in compression and relaxation of the blood, influencing the optical properties of the blood. Further analytical studies are required before any definite conclusions can be drawn regarding this peculiar phenomenon.

The variability of k represents the multifactorial biological process of RBC aggregation, which differs from a simple chemical process involving combination of two substances. The initial high value of k for feline blood (FIG. 11, open circles) indicated that the velocity of RBC aggregate formation was maximal when abundant individual cells were readily available nearby. However, it slowed down with formed aggregates since the larger the aggregates became, the smaller was the chance of colliding with each other and the smaller was the attractive force due to the widened inter-aggregate distance. To a certain extent, this explanation may be applied to the increase in $k_2$ with hematocrit. The organization and ordering of red blood cells in space resembles a decrease in entropy in thermodynamics, whereas their dispersion, disorganization, and randomization resembles an increase in entropy, although the spontaneity is just opposite in direction due to the attractive force between red cells. The low value of k in the initial part for human blood (FIG. 11 closed circles) may be explained by species differences of red cell shape and flexibility, by which the aggregation process is somehow prevented in the change from a random state to orientation-ordering ready to aggregate.

Since RBC aggregation represents one of the essential biological processes involving red blood cells in both the ex vivo and in vivo situation (except for blood of certain species, like bovine blood), the densitometer head as a whole blood RBC aggregometer (FIGS. 3 and 4) is considered to have a potentially wide usefulness. We have preliminarily employed it as a warning apparatus for flow disturbance in an extracorporeal system of blood circulation, and as a monitor of stop and flow of blood through arteries and veins in situ (see paper entitled "Application of whole blood RBC aggregometer to the carotid artery, jugular vein, and femoral vein in cats" presented by Tanahashi, N., F. Gotoh, M. Tomita, and M. Kobari at the International Congress of Angiology, 1985, (Abstract)).

Heretofore, I explained a "whole blood RBC aggregometer" which measured the RBC aggregation rate of blood freshly drawn from patients (see paper entitled "Whole blood RBC aggregometer for human and feline blood" by Tomita, M., F. Gotoh, N. Tanahashi, and P. Turcani, American Physiological Society 1986). The principle of the RBC aggregometer was based on the photometry of changes in the optical properties of whole blood in a tube in association with aggregate formation of red blood cells. RBC aggregation (rouleaux formation in the strict sense) represents one of the common physiological and reversible biological processes involving red blood cells (except for blood of certain species such as the ox and sheep) and RBC aggregation is one major cause of viscosity changes of blood with shear (see for example Benis and Lacoste, supra, and Chien et al, supra). It is expected therefore that some hemorheological information on flowing blood, or at least "stop or flow" information indistinguishable with the naked eye, can be obtained with an RBC aggregometer head when it is applied directly to tubes containing whole blood or unopened vessels in situ.

Next, I will demonstrate such applicability of the RBC aggregometer head in experimental animals, as well as its practical usefulness in clinical medicine.

Figure 13:
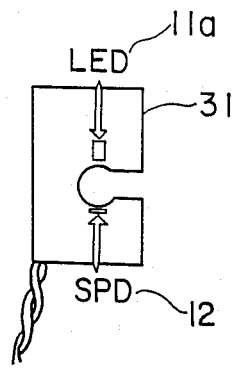
FIGS. 13, 14 and 15 are diagrams of several types of densitometer heads, FIGS. 13, 14 and 15 showing respectively fixed type, slide-in type and clip type heads.
Figure 14:
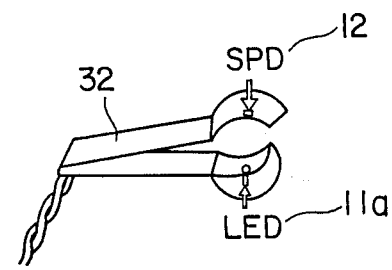
Figure 15:
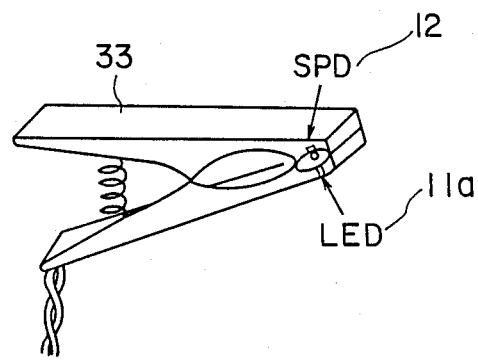

The RBC aggregometer head used for the present experiments was modified from the original device as follows. As reported previously (see Tomita, Gotoh, Tanahashi and Turcani, supra), it consisted of a small light source and a small photo-sensitive element. The light source was a gallium arsenide diode which emitted infrared light (light emitting diode (LED), $\lambda = 940$ nm, Hamai Electric Co., Tokyo). The diode was sealed in a small glass bulb which formed a convex lens at the top. This lens gathered the emitted light into a light beam, which was directed to the center of the tubes or vessels in situ to be studied. The choice of wavelength in the infrared range has made it possible to apply the RBC aggregometer head to tube or vessel in situ having a diameter of 0.6 cm (ID). The photo-sensitive element was a silicon photodiode (SPD-550, Sharp Electric Co., Tokyo), a kind of solar battery, with a narrow, photo-sensitive surface area of only 0.05 cm by 0.3 cm. The LED bulb and SPD were arranged facing each other, interspaced by flowing blood in a transparent vinyl tube, or vessel in situ, so that any change in LT of the whole blood was readily detectable. Modifications were made in the arm holding the LED and SPD so that it was possible to attach or detach it easily to or from different sizes of tubes or vessels in situ without any damage to the tubes or vessels. Several types of RBC aggregometer head were manufactured: a fixed type, alligator clip type, wide mouth clip type, slide-in type, pincette type, adjustable holder type, etc., some of which are illustrated in FIGS. 13, 14 and 15. Electrical circuits were devised so that 1.2 volts was applied to the LED and the output of the SPD was fed directly to a DC recorder 15 (FIG. 6) (Rikadenki, Tokyo) with a parallel resistance of 5K ohms for continuous recording of LT. FIG. 13 shows a fixed type comprising a support member 31 with a U-shaped hole having a gallium arsenide diode (LED) 11a and a silicon photodiode (SPD) 12. FIG. 14 illustrates a slide-in type comprising a support member 32 formed by folding an elongated resilient brass plate of which ends are provided with LED 11a and SPD 12. FIG. 15 shows a clip type 33 of which ends are formed with LED 11a and SPD 12.

Three levels of flow experiments were performed with the RBC aggregometer head. First, fundamental flow experiments were carried out in a transparent vinyl tube of 0.26 cm ID, 0.40 cm OD and 1 m in length. Heparinized whole blood samples freshly drawn from 3 healthy human volunteers (Hct 45%) were introduced, respectively, into the one end of the tube from a reservoir placed at a higher position, and a surgical clamp was applied to the tube to stop the blood flow. A graded flow of blood was imparted by controlling the height of the reservoir. An alligator clip type of RBC aggregometer was attached at the middle of the tube, and a photoelectric drip counter and a 50 ml Mess-cylinder were set at one end of the tube for measuring the relative and absolute flow rates, respectively. Investigations were made of the flow effect, relationship between flow rate and changes in LT, and reproducibility of the changes in LT with flow. In these experiments, by assuming whole blood to be a Newtonian fluid (although this was, as I was aware, strictly erroneous), a rough value of the wall shear rate $\gamma_w$) was calculated on the basis $\gamma_w = Q/2\pi D^3$, where D was the inner diameter of the tube and Q the blood flow. The RBC aggregometer head was then applied to vessels in vivo. I found it handy and easily attachable and detachable in the case of the slide-in type, the arm of which was constructed simply from a thin elastic rectangular piece of metal plate folded in the middle. For the in vivo experiments, 6 cats of both sexes weighing 3.2–4.1 kg were used under general anesthesia with 50 mg/kg body wt of alpha-chloralose and 500 mg/kg body wt of urethane and immobilization with alcuronium chloride. Respiration was controlled with a Harvard respirator. The carotid artery in 2 cats, the jugular vein in 3 cats, and the femoral vein in 1 cat were exposed, respectively, preserving the adventitia as far as possible. The RBC aggregometer head was put in place and the lead wires were fixed to the nearby skin with surgical thread. An electromagnetic flowmeter (Nihon Kohden, Tokyo) was also mounted on the carotid artery and jugular vein near the aggregometer head to monitor the mean blood flow (EMF). Arterial blood flow was stopped by compression of the vessels with a surgical clamp covered with a plastic material at the tips to protect against damage of the vessels. The venous blood flow was increased by intravenous administration of papaverine in the case of the jugular vein, or muscle massage in the case of the femoral vein. At attempt to minimize the effect of diameter changes was made by securing the vessels tightly in the receptacle of the aggregometer head with slight compression so that the vessels were transformed to a slightly ellipsoid shape in the cross sectional plane. To ascertain that the LT change was not due to diameter change, clamping was performed at both the upstream and downstream ends of the vessel with respect to the site where the RBC aggregometer head was placed.

The possible clinical applicability of the RBC aggregometer head was tested in the cat, by hooking the alligator clip type to a tube which connected directly between a femoral artery and a femoral vein. This A-V shunt was closed by clamping at the venous end using a surgical clamp, and the resultant change in LT was recorded. Finally, practical application of the RBC aggregometer head (wide-mouth clip type) was made in a clinical case (24 year old male patient) with renal failure. The wide-mouth clip type was hooked to a tube connecting the patient's brachial artery to the dialyzer. A temporary stoppage of blood flow was effected by clamping the arterial side of the tube, and then the venous side, while the LT change was continuously recorded.

Figure 16:
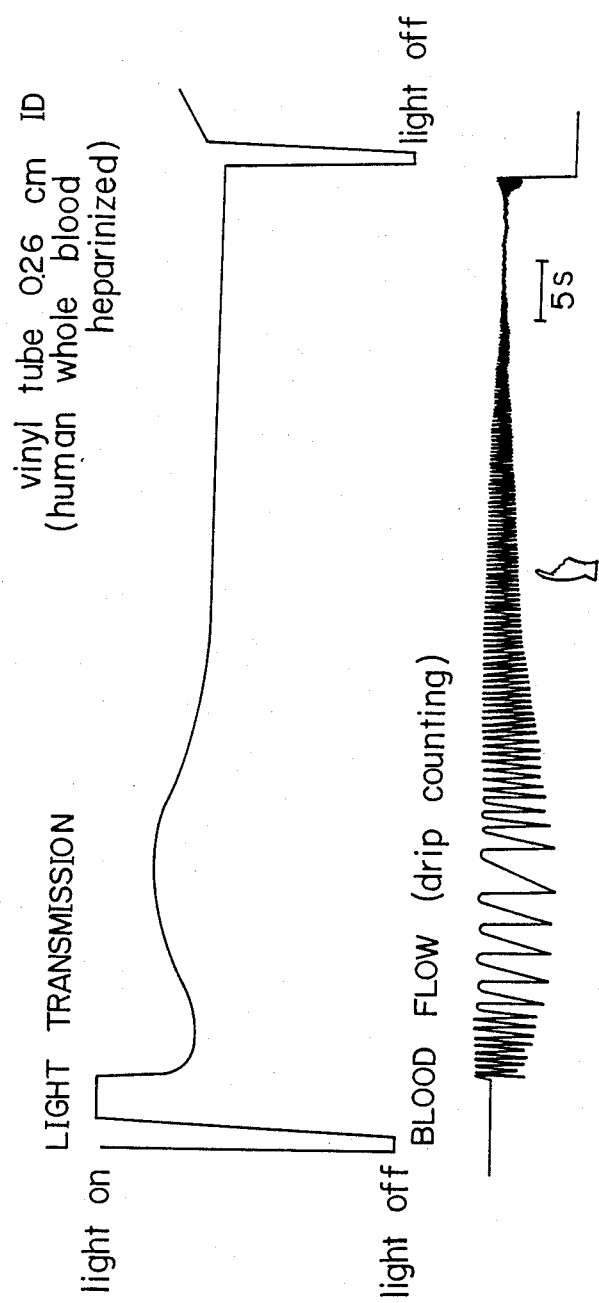
FIG. 16 is a diagram illustrating the flow effect in the light transmission of blood in a tube.
Figure 17:
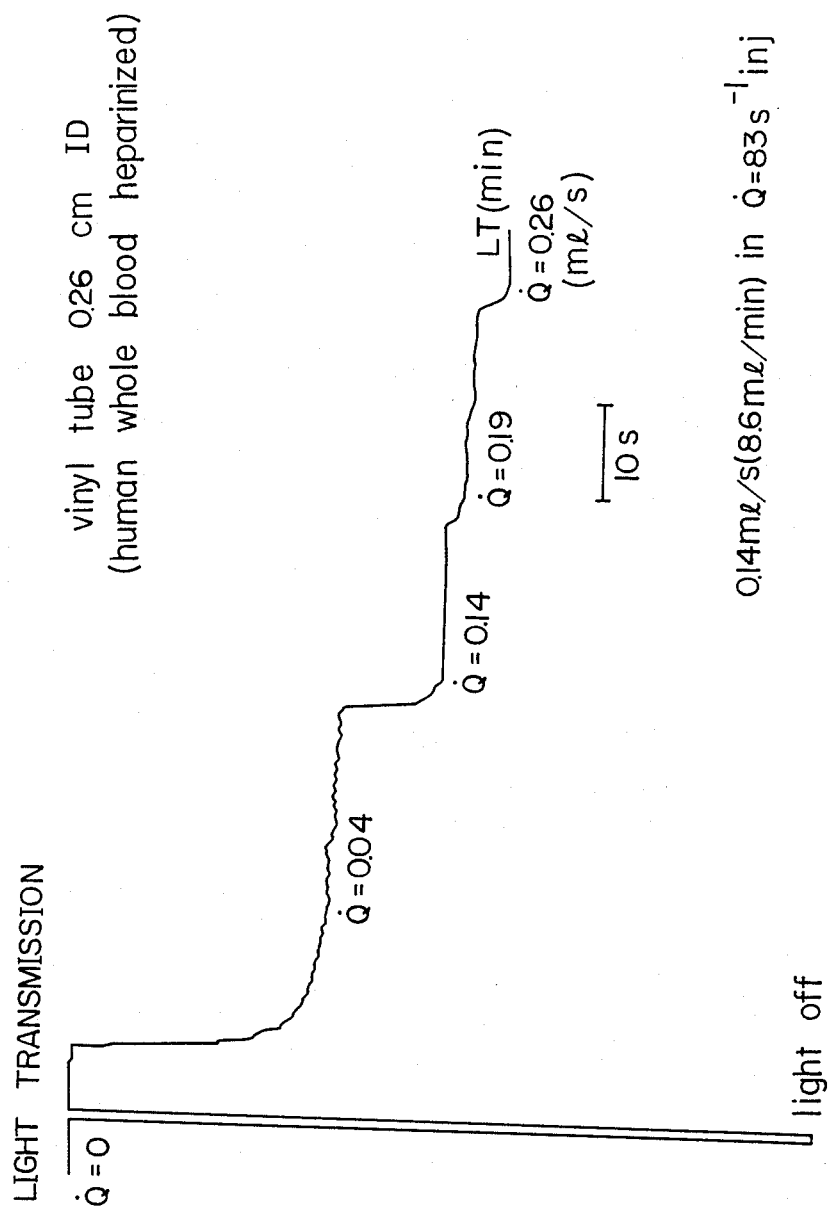
FIG. 17 is a diagram illustrating stepwise increases in flow rate resulting in stepwise decreases in light transmission.
Figure 18:
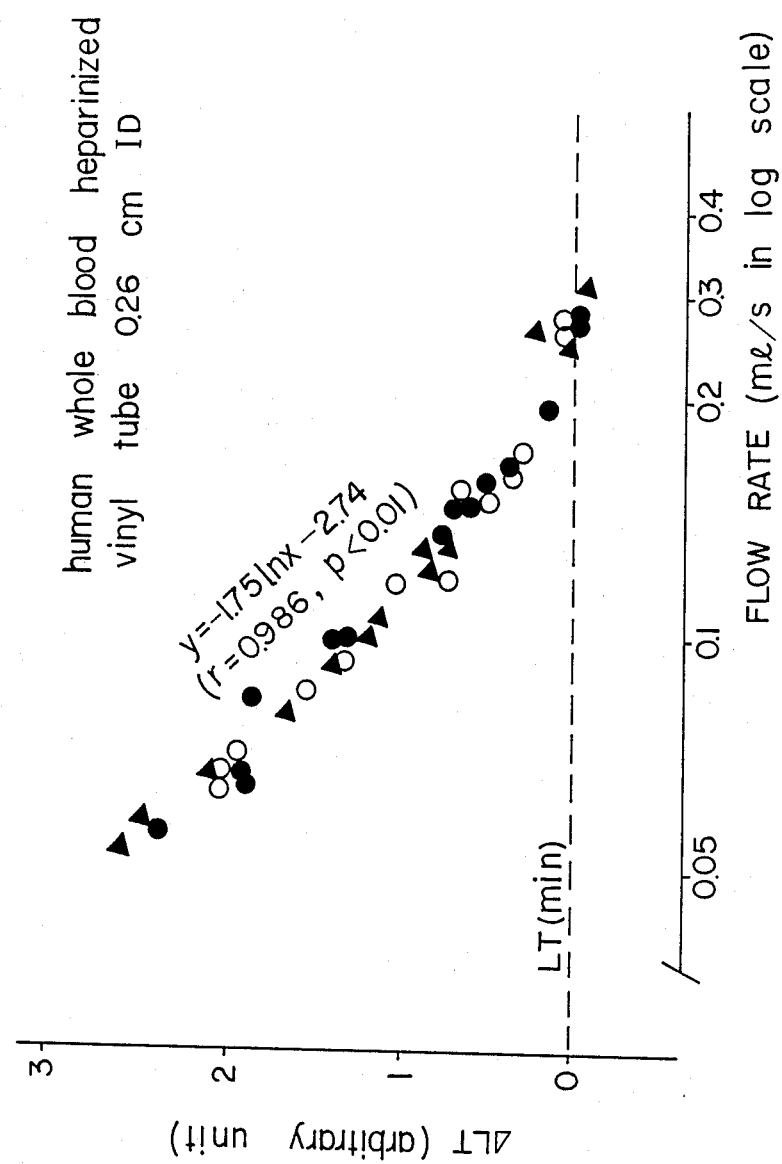
FIG. 18 is a diagram illustrating the relationship between shear rate and light transmission (LT) adjusted at the LT (max) level.
Figure 19:
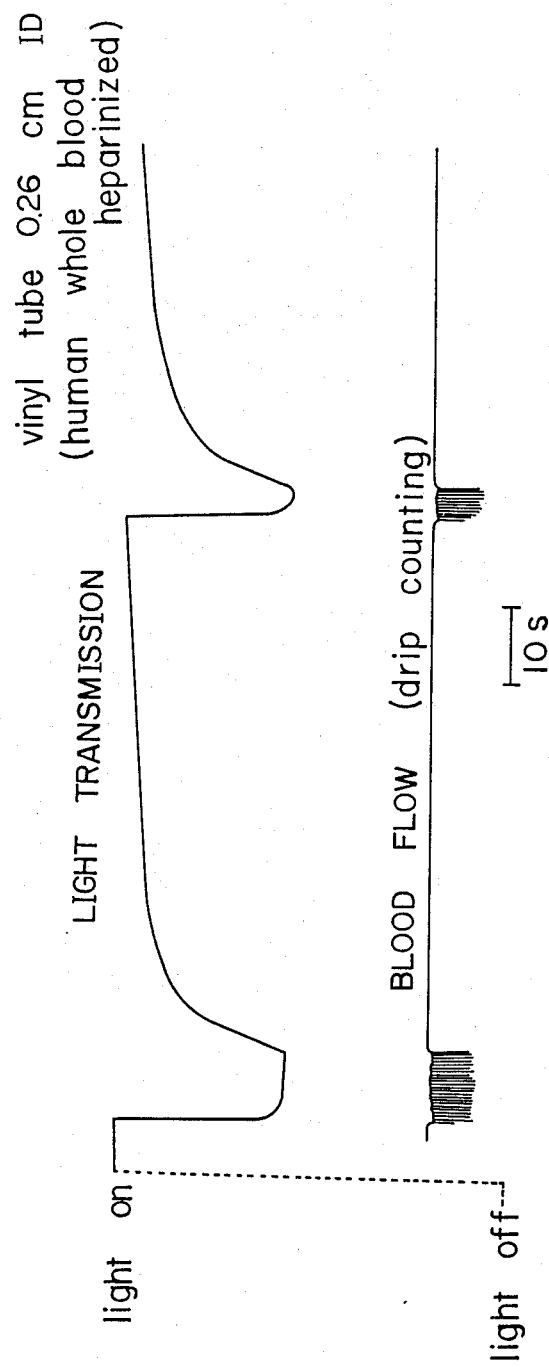
FIG. 19 is a diagram showing reproducibility in changes of LT with repeated flows.

FIG. 16 shows a continuous recording of the LT of human whole blood during changes in flow rate induced by lowering or elevating the blood reservoir. Calibration of LT was carried out by switching off the LED light source; this can be seen at both ends of the record as a downward deflection indicated by "light off". When the whole blood was allowed to flow at the arrow, a sudden decrease in LT from LT(O) (the low condition will be indicated in parentheses hereafter) was observed. The LT record subsequently chased after, with some delay, the blood flow changes which were indicated by the frequency of oscillation of the record by the drip counter. However, above a certain flow rate at the finger in FIG. 16, the LT record reached bottom (LT(max)) and became unchanged in spite of any further increase in flow rate. When the flow rate was increased in a stepwise fashion by such successive procedures as rapidly elevating the reservoir and holding it at a certain level, stepwise decreases in LT were observed. FIG. 17 shows the decreases in LT from LT(O) when the flow rates were successively increased to 0.04, 0.14, 0.19 and 0.26 ml/s (the corresponding wall shear rates were approximately 22, 80, 105, and 140/s, respectively). A hysteresis phenomenon in LT was noted during the procedure of returning the reservoir to the previous zero-flow level. A summary of the relationship between LT and shear rate (3 human whole blood samples) is presented in FIG. 18, where the difference in LT from LT(max) is plotted against the logarithm of flow rate. The graph reveals that a linear relationship existed between the two in the range from 0.05 ml/s to 0.3 ml/s (approximately 20/s to 180/s as wall shear rate). For flow values lower than 0.05 ml/s, the relationship was not examined because of the limitation in the accuracy of the drip counter. The regression line was LT=1.75×lnQ−2.74, and the correlation (r=−0.986) was statistically significant (p<0.01). The reproducibility in the values of LT(max) with repeated flow procedures was within approximately 5% (FIG. 19).

APPLICATION OF THE RBC AGGREGOMETER HEAD TO VESSELS IN SITU

Figure 20:
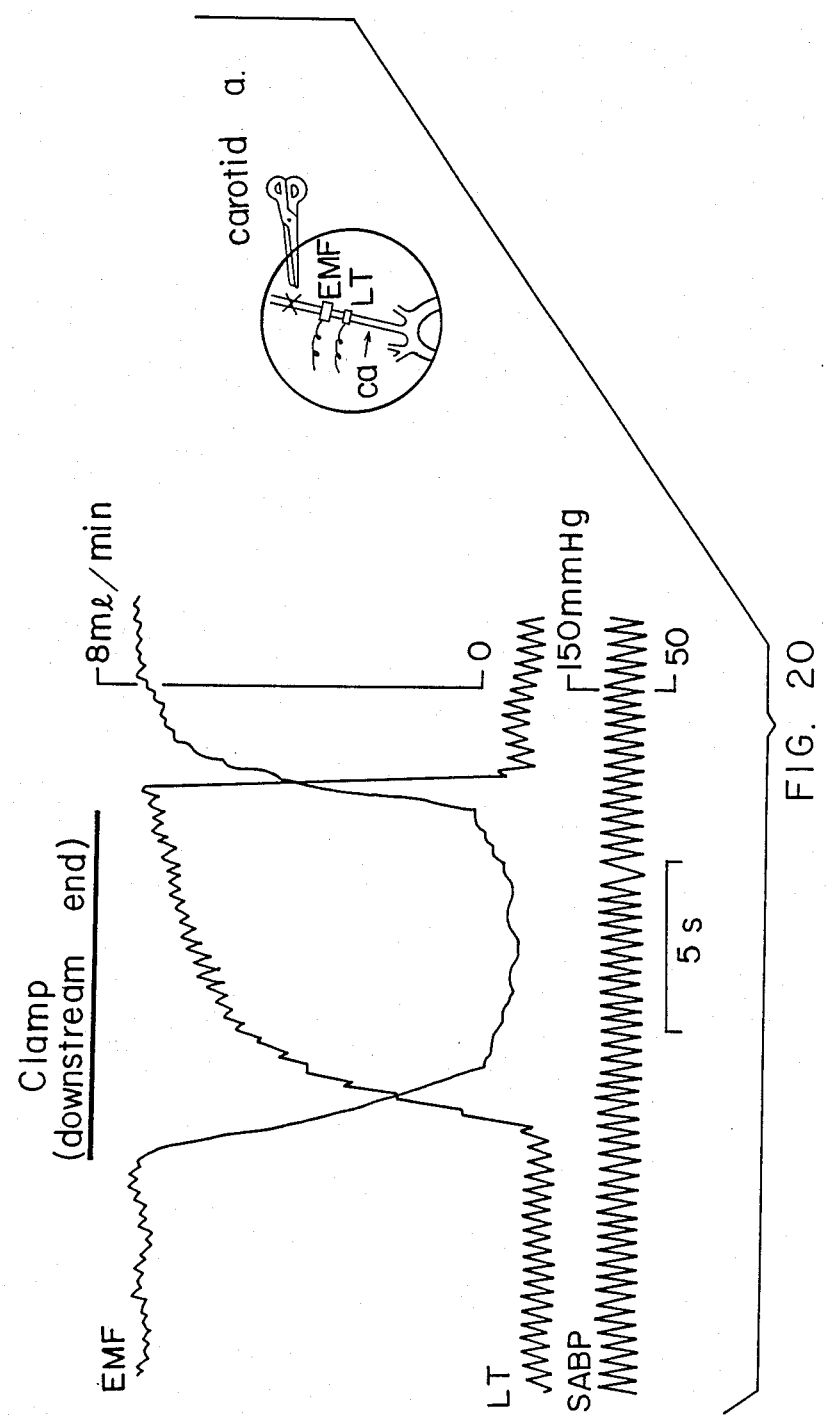
FIG. 20 is a diagram which shows the slide-in type RBC aggregometer head and electronic magnetic flow (EMF) probe attached to the carotid artery in a cat and which also shows mirror changes in EMF and LT of the carotid artery during the clamp-on and -off procedures at the downstream end of the artery.
Figure 21:
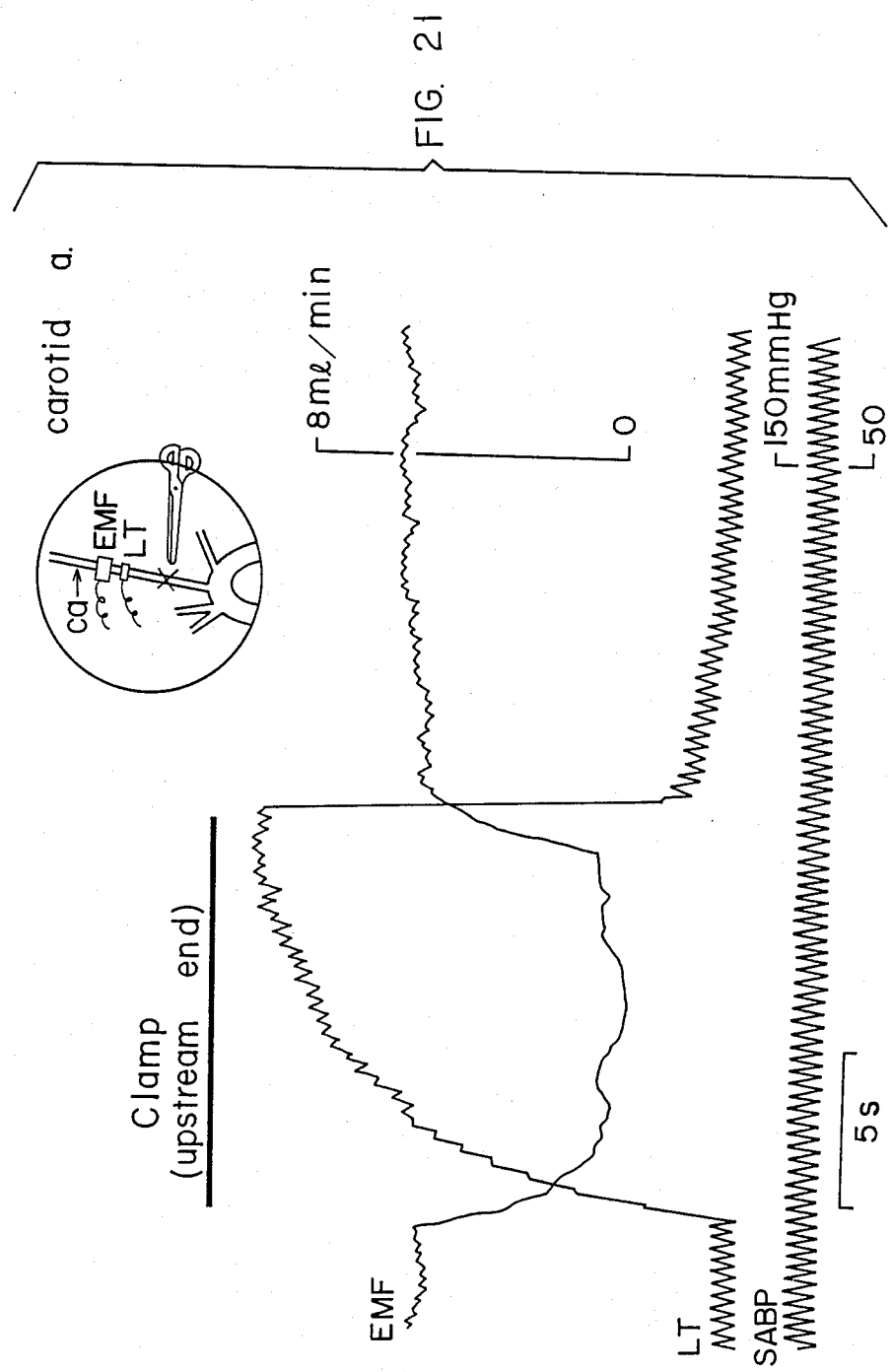
FIG. 21 is a diagram similar to FIG. 20 with the clamp at the upstream end of the carotid artery.

Carotid artery: FIG. 20 shows an actual protocol of continuous recordings of LT and EMF through the carotid artery during stoppage of blood flow by clamping the downstream end of the artery to the site where the RBC aggregometer head (slide-in type) was placed. A dramatic increase in LT which mirrored the decrease in blood flow (EMF) was observed on occluding the carotid artery (clamp-on curve), and a rapid recovery in LT occurred after release of the clamp (clamp-off curve). It should be noted that the speed of the upward deflection upon stoppage was rather slow being approximately 3.5 s as half time (=0.198 as rate constant ($k_{10}$), while that upon release was extremely rapid being less than 0.1 s as half time. Similar changes were reproduced during clamping the upstream end of the artery (FIG. 21).

Figure 22:
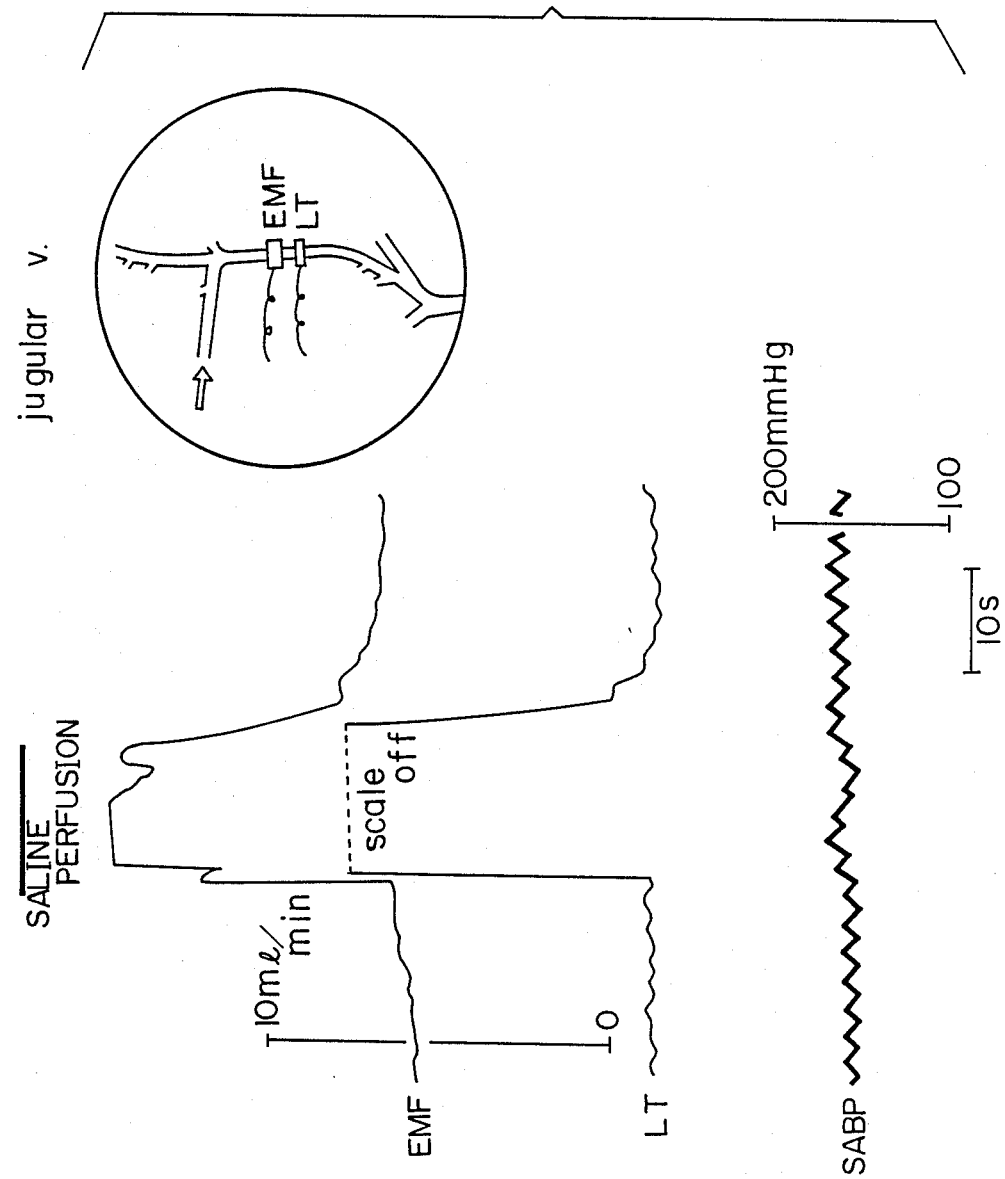
FIG. 22 is a diagram which shows a test of applicability to the jugular vein wherein, to confirm appropriate attachment of the slide in type RBC aggregometer head and EMF probe, saline was injected into the venous branch located upstream.
Figure 23:
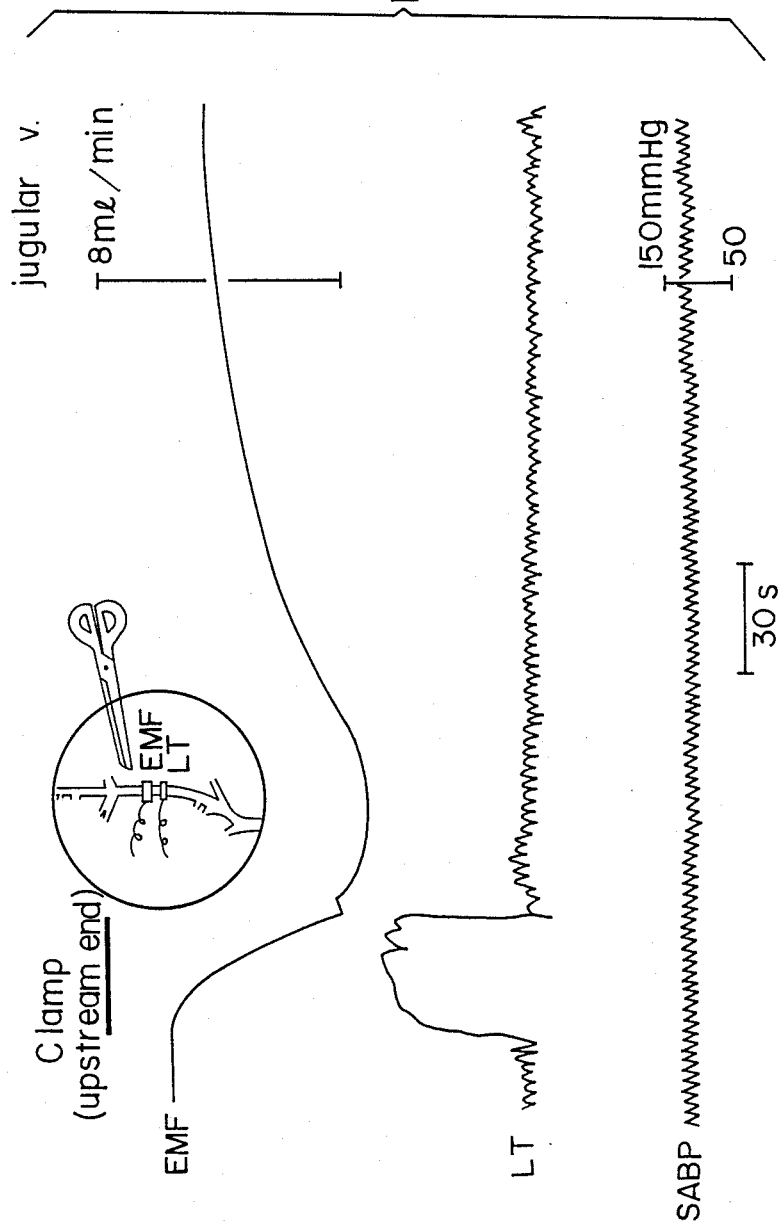
FIG. 23 is a diagram which shows that transient upstream occlusion of the jugular vein produces a similar change in LT to that observed in the carotid artery.
Figure 24:
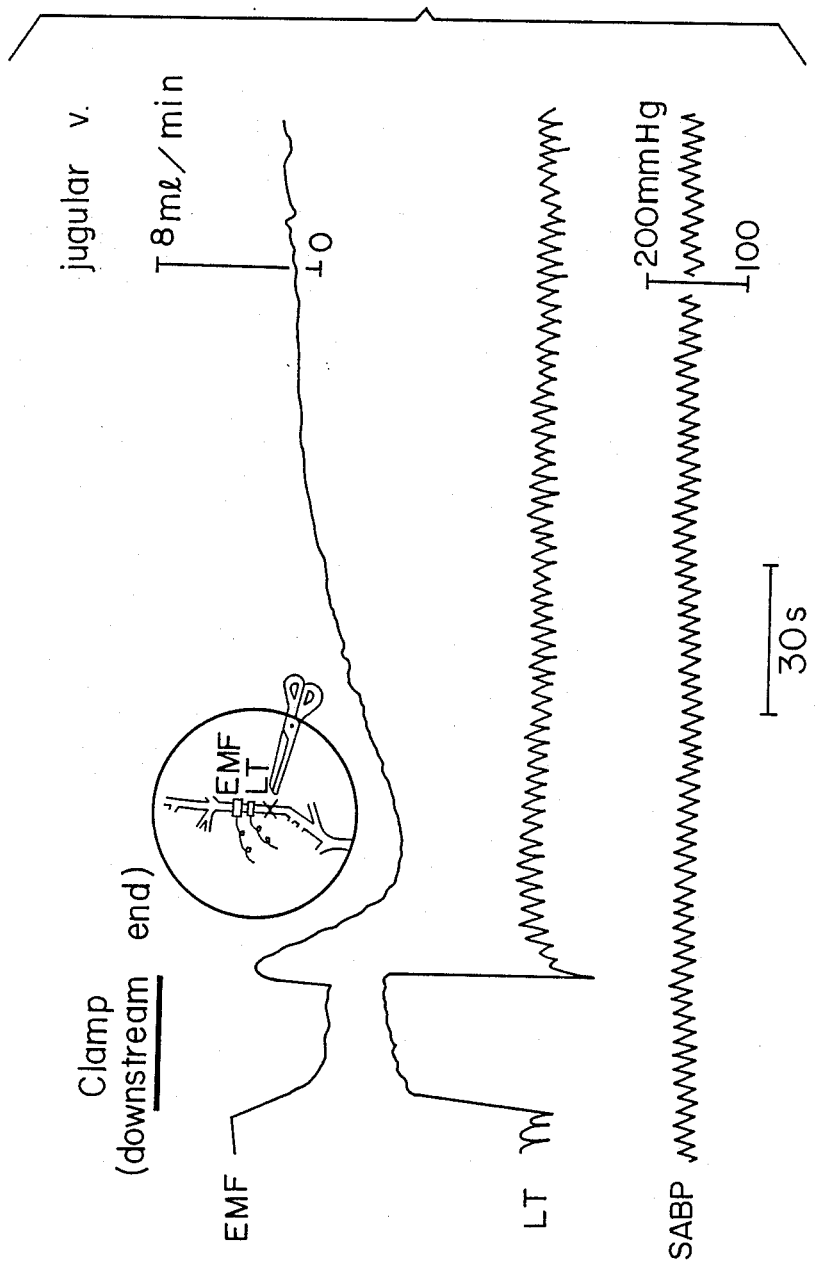
FIG. 24 is a diagram of record for downstream occlusion illustrating the peculiar flow change to below zero in the jugular vein after release of the clamp.

Jugular vein: The slide-in type RBC aggregometer and the electro-magnetic flow probe were applied to the jugular vein; however, such application was found to be rather difficult because of the softness of the vein. Prior to occlusion, appropriate attachment of the sensors to the vein was confirmed by vigorous saline injection into the venous branch upstream from the measuring site during continuous recording of LT and EMF. The result was an immediate increase in both LT and EMF as shown in FIG. 22, indicating hemodilution and a markedly increased flow. Subsequently, the jugular vein was occluded at the upstream end using a surgical clamp. LT then revealed almost the same change as in the case of the carotid artery (FIG. 23), i.e., an increase with a half time of ca. 3.5 s upon clamping and a rapid recovery upon release. However, the flow changes in response to the occlusion were slow and lagged behind. Unlike LT, the EMF record continued to decrease even after release of the clamp, reaching the zero level in 3 min, and then began to show an extremely slow recovery. The discrepancy between the changes in LT and EMF became more marked when the vein was clamped at the downstream end as illustrated in FIG. 24. The LT change was the same as in the case of upstream clamping, but the EMF showed a delayed, and indeed peculiar, biphasic change: after release of the clamp, EMF tended to recover once, but then began to decrease to much lower than the zero-flow level, suggesting that the flow was reversed.

Figure 25:
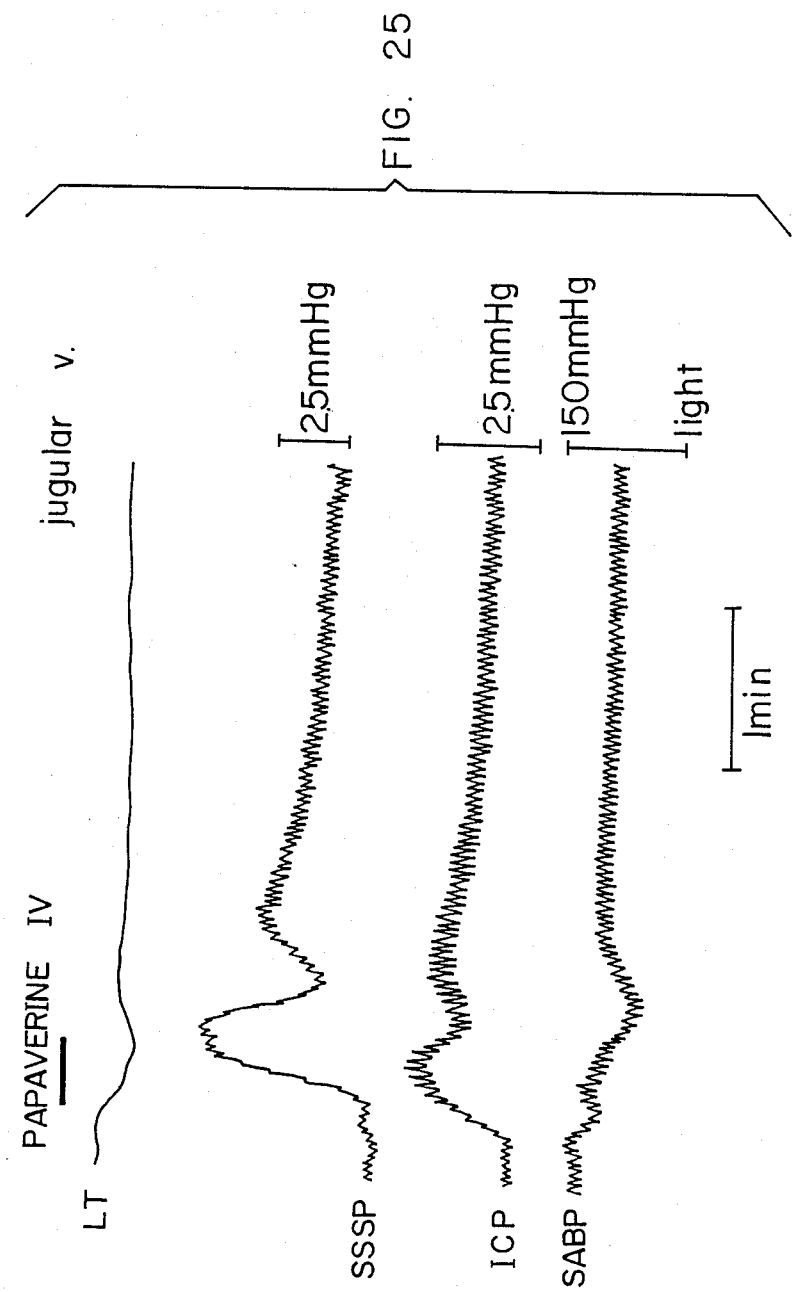
FIG. 25 is a diagram which shows decrease in LT of the jugular vein when papaverine hydrochloride was administered intravenously, in this case, concomitant recordings of the superior sagittal sinus pressure (SSSP) and intracranial pressure (ICP) were made.
Figure 26:
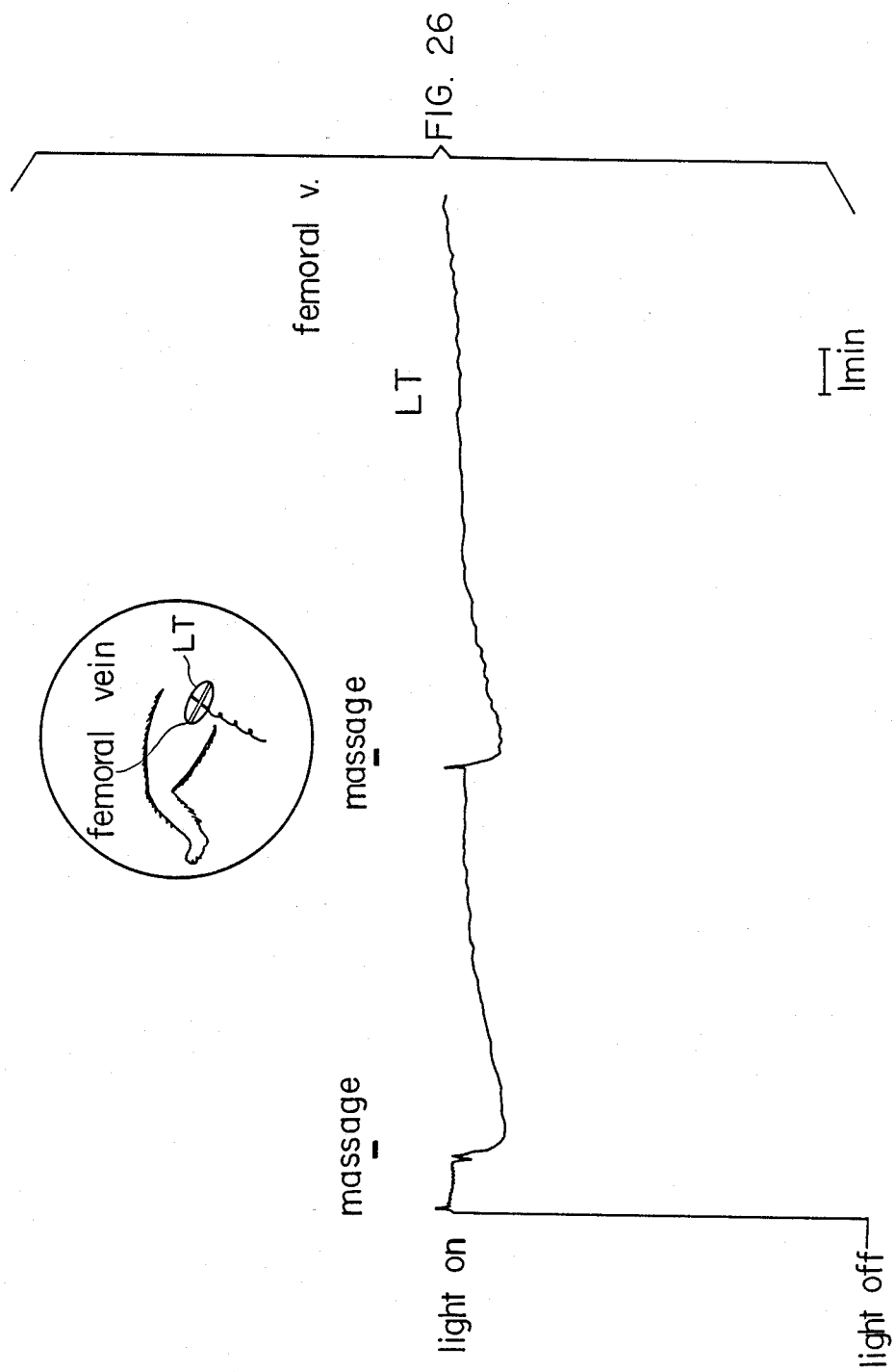
FIG. 26 is a diagram of the case where RBC aggregometer head is applied to the femoral vein of a cat showing decrease of LT due to repeated massage of quadriceps muscle.

In other experimental series using cats where LT together with the intracranial pressure (ICP) and the wedge pressure of the superior sagittal sinus (SSSP) were continuously recorded, the jugular flow was subjected to increase by papaverine administration. As shown in FIG. 25, LT revealed a decrease, which suggested disaggregation of red blood cells in the venous blood with a possible increase in flow. Femoral vein: The slide-in type RBC aggregometer head was applied to the femoral vein of the cat. In this case, blood flow was increased by massaging the quadriceps muscle through which the blood had perfused. LT revealed a decrease (FIG. 26) similar to the case of the LT change in the jugular vein during and after papaverine administration. The decrease was reproduced with repeated massage.

Figure 27:
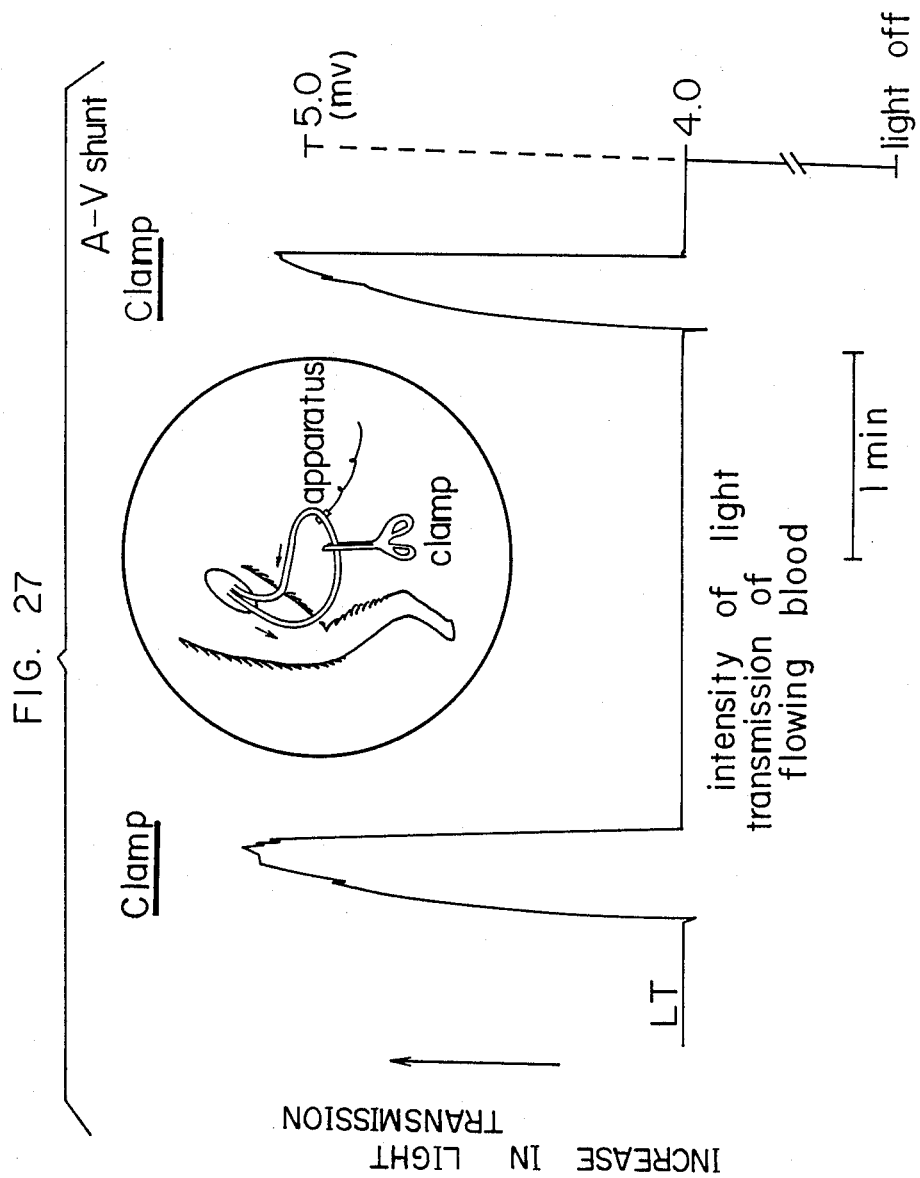
FIG. 27 is a diagram which shows flow stop of whole blood in an arterio-venous shunt tube detected with the BBC aggregometer head.

A-V SHUNT AND EXTRACORPOREAL CIRCULATION: FIG. 27 showed a rapid increase in LT when the RBC aggregometer head of alligator clip type was hooked to an A-V shunting tube in the cat, and flow was stopped by clamping on. The same change was observed when the wide-mouth clip type was applied to the tube of the extracorporeal system in a patient with renal failure as illustrated in FIG. 28. The signal obtained at flow stop was sufficiently large to trigger the ringing of a buzzer and turning on of a red flashlight, by which attention could be drawn to the disturbance of circulation in the system.

In the ex vivo experiments, LT was found to decrease linearly with the logarithm of flow increases upto 180/s as shear rate, above which the LT record formed a plateau indifferent to flow changes. The major part of descending slope could be explained by shear dependent formation of RBC aggregates, which resulted in changes in the optical properties of the whole blood (see Brinkman et al, supra, and a paper by Klose, H. J., E. Volger, H. Brechtelsbauer, L. Heinich, and H. Schmid-Schönbein entitled "Microrheology and light transmission of blood. I. The photometric effects of red blood cell aggregation and red cell orientation." Pflügers Arch. 333:126-139, 1972). The finding that LT converged to a certain value at a flow rate below 20 ml/s (180/s as wall shear rate) as shown in FIG. 17, would suggest that an equilibrium was established at that flow rate between the magnitude of the shearing force which tended to split the RBC aggregates, and the force keeping the RBC together. However, when the flow rate exceeded a certain threshold, all of the aggregated RBCs became so completely dispersed, that no further change in LT through RBC aggregation could occur. This was represented by the plateau part as shown in FIG. 16 and FIG. 18, which was consistent with previous observations (FIG. 12) except for the higher value of the threshold in the present study. However, the plateau part disagrees with the observation of Klose et al, supra, who found that the light transmission of human whole blood measured by their rheoscope initially decreased with shear in the same manner as observed by me, but subsequently began to increase above a certain threshold of shear rate. They attributed the increase in LT with shear to RBC deformation aligned to stream-lines of blood flow. On the other hand, the plateau demonstrated above indicated that such alignment appeared to exert little effect on LT in the present tube method. This was supported by the lack of initial upstroke at the beginning of the clamp-on curves (FIGS. 20, 21, 23 and 24) or, if any, the minimum appearance of upstroke (FIGS. 27 and 28). The initial upstroke on "syllectograms" observed by Brinkman et al, supra, and by Schmid-Schönbein, H., K. A. Kline, L. Heinich, E. Volger, and T. Fischer in a paper entitled "Microrheology and light transmission of blood. III. The velocity of red cell aggregate formation.", Pflügers Arch. 354:299-317, 1975, was ascribed by them to rapid randomization in the orientation of aligned RBCs and recovery of the deformed shape at the moment of deprivation of shearing force. It would appear likely that the centrifugational force which would affect dispersed individual RBCs during the rotational shear involved in their methods, could cause an uneven distribution of RBCs and therefore a spatial gradient in hematocrit at high shear rates, which led to in changes in light transmission with shear. Whatever the mechanism might be, such high-flow-cutoff characteristics in the LT of the RBC aggregometer head as seen in FIG. 18 would tend to limit its practical usefulness as a flow sensor. I also found in other experimental series employing a tube of the same dimensions as in the present set-up for the in vitro experiments that changes in LT were closely related to changes in the apparent viscosity of flowing whole blood, where the apparent viscosity was simultaneously determined with a capillary, viscometer which measured the flow rate and pressure difference at two sites along the tube using a differential transducer (see a paper by Tanahashi, N., M. Tomita, T. Sato, T. Amano, T. Tanaka, and F. Gotoh entitled "New capillary viscometer designed to eliminate end effect" (Abstract), Biorheology 16:483, 1979). It was concluded that what was recorded with the RBC aggregometer head would tend to be mainly RBC aggregation of the whole blood in tubes or vessels in situ, the changes of which were suggestive of relative changes in the apparent viscosity of the blood in the tubes or vessels.

Thus, the RBC aggregometer head may be employed as a "whole blood RBC aggregometer" not only ex vivo (see Tomita, Gotoh, Tanahashi and Turcani, supra) but also in situ. When the LT changes in association with flow changes were analyzed by a closer inspection, a certain time delay in LT behind the flow changes was observed (FIG. 16). This delay was most apparent when flow was stopped all at once (FIGS. 20 and 21). The delay was attributed to the time spent for RBC aggregate formation in the vessels in situ. The half time of the clamp-on curve was approximately 3.5 s, which agreed well with the value of 0.192/s in $k_{10}$ (3.6 s as half time) obtained in ex vivo studies on feline whole blood reported previously (see Tomita, Gotoh, Tanahashi and Turcani, supra). On the other hand, the LT change upon resumption of blood flow was extremely fast with a half time of less than 0.1 s, which was the time for sudden destruction of the RBC rouleaux network structures. These findings suggest that the RBCs began to aggregate intravascularly with slowing down of the blood flow even in vessels in situ, so confirming Weis-Fogh's observation in his thesis entitled "Aggregation of erythrocytes in small vessels" Copenhagen, 1957 (cited from W. G. Zijlstra and S. G. Heeres, Proc. Kon. Ned. Akad. Wet., Ser. C. (Biol. Med.) 68:412–423, 1965) that intravascular rouleaux formation occurred whenever the speed of flow and shearing forces fell below normal. The results for the carotid artery (FIGS. 20 and 21) could be explained by the findings of the ex vivo experiments.

The decrease in LT of the femoral vein with muscle massage, and of the jugular vein with intravenous administration of papaverine hydro-chloride, could be attributed to an increase in blood flow and subsequently RBC disaggregation. This led to the speculation that the shear rate of the venous blood was less than 180/s, positioning the venous hemorheological situation on the slope of FIG. 18. In other words, RBCs in the blood of these veins appeared to be partly aggregated even under physiological conditions. However, the venous data from the jugular vein (FIGS. 23 and 24) were difficult to explain adequately by such a straightforward schema of shear-dependent RBC aggregation as envisaged above, since they revealed a discrepancy between the LT change and flow change. This could represent a simple artifact arising from changes in the delicate electrical contact between the electrodes of the magnetic flow probe and the venous surface due to shrinkage of the vein since occlusion was carried out at the upstream end. However, this possibility was excluded when the occlusion was made at the downstream end of the jugular vein and the part of the vein assumed to be slightly coarctate. Since the rate of RBC aggregation-disaggregation was entirely shear dependent, there was necessarily a dissociation between the magnitude of the interlaminar shearing force in the venous blood and the total flow change of the venous blood, which indicated deviation from Poiseuille's flow. Unlike in rigid tubes, the mass of RBC aggregates would continue to move by inertia and the high compliance ($\Delta V/\Delta P$) of the venous system even under circumstances deprived of driving force from the heart. In FIG. 24, LT shows exactly the same change as in the above experiments while EMF reveals a below-zero flow after release of the occlusion. The below-zero flow detected by the electromagnetic flowmeter could be interpreted as a reversed flow. On the basis of such a peculiar hemo-rheological condition in which the interlaminar shear of the blood was continuously high and yet flow was reversed, I assume the existence of "invaginated flow", in which double layers of positive and negative shear forces existed at zero flow as a whole. I cannot arrive at any definite conclusion from the present rather fragmental data, but I understand that the results have demonstrated the applicability of the RBC aggregometer head for studying complicated anomalous venous flow from the hemorheological standpoint of RBC aggregation and therefore the possible apparent viscosity of the flowing blood together with simultaneous measurement of parameters such as flow, perfusion pressure, and vessel diameter.

An additional application of the RBC aggregometer was for detecting the "stop or flow" phenomenon of whole blood in a tube, which could not be distinguished with the naked eye. As seen from the records in FIGS. 27 and 28, a stop of flow produced a large signal which could operate a voltage comparator switch. Thus, the RBC aggregometer may find usefulness as a warning device for disturbances of flow in an extracorporeal circulatory system such as in renal dialysis, or artificial cardio-pulmonary apparatus. Further possible applications may arise in vascular surgery where the patency of an operated or grafted vessel needs urgently to be checked.

The simple device of a densitometer head consisting of an infrared emitting diode and a silicon photodiode, which was attached to a transparent vinyl tube, was used as a whole blood RBC aggregometer. Freshly drawn heparinized whole blood was introduced into the tube and a shear of ca. 500 $s^{-1}$ was applied with a solenoid. Following full stop of the blood flow, an "RBC aggregogram" (subsequent changes in optical density of the blood) was recorded. It exhibited an initial rapid rise and subsequent decline in association with RBC aggregation. Assuming that the beginning of the decline was monoexponential, the rate constant was calculated by a special mathematical procedure from two values obtained at 10 and 20 s on the RBC aggregogram. This rate constant for the 10 s value ($K_{10}$) was arbitrarily termed the RBC aggregation rate of the blood.

It is concluded that the simple, low cost densitometer head of the whole blood RBC aggregometer explained here ex vivo can be used clinically as a routine check for RBC aggregability.

The above described embodiments, of course, are not to be construed as limiting the breadth of the present invention. Modifications, and other alternative constructions, will be apparent which are within the spirit and scope of the invention as defined in the appended claims.

What is claimed is:

1. An apparatus for measuring the aggregation rate of whole blood red blood cells, comprising:
   a tube through which blood can flow;
   means for varying flow rate of the blood in said tube;
   means, at one side of said tube, for transmitting light through the tube and the blood therein;
   means for detecting light from said light transmitting means after the light has been transmitted through the blood in the tube, and for producing signals representative of changes in optical density of the light so detected at different flow rates of the blood;
   means for receiving said signals to determine said aggregation rate;
   said tube comprising a cubital vein in an extracorporeal circulatory system;
   said detecting means comprising a light detector of a densitometer; and
   said densitometer being connected to a voltage comparator switch of a warning device.

2. The apparatus of claim 1, wherein said extracorporeal system is a renal dialysis.

3. The apparatus of claim 1, wherein said extracorporeal circulatory system is an artificial cardiopulmonary apparatus.

4. An apparatus for measuring the aggregation rate of whole blood red blood cells, comprising:
   a tube through which blood can flow;
   a syringe for containing a sample of the blood, the syringe being connected to said tube and in communication with the interior of said tube, said syringe having a movable piston therein to effect flow of blood in said tube;
   a solenoid having a plunger connected to said piston for moving said piston along said syringe;
   electrical circuit means for controlling supply of electrical power to said solenoid for controlling the rate of movement of said piston in one direction;
   means for bringing said piston to a full stop after movement thereof in said one direction;
   means, at one side of said tube, for transmitting light through the tube and the blood therein;
   means for detecting light from said light transmitting means after the light has been transmitted through the blood in the tube, and for producing signals representative of changes in optical density of the light so detected at a controlled flow rate of the blood and when the flow of blood is stopped by said bringing said piston to said full stop;
   means for receiving said signals to determine the aggregation rate of the red blood cells; and
   said light transmitting means comprising a semiconductor laser.

5. An apparatus for measuring the aggregation rate of whole blood red blood cells, comprising:
   a tube through which blood can flow;
   a syringe for containing a sample of the blood, the syringe being connected to said tube and in communication with the interior of said tube, said syringe having a movable piston therein to effect flow of blood in said tube;
   a solenoid having a plunger connected to said piston for moving said piston along said syringe;
   electrical circuit means for controlling the supply of electrical power to said solenoid for controlling the rate of movement of said piston in one direction;
   means for bringing said piston to a full stop after movement thereof in said one direction;
   means, at one side of said tube, for transmitting light through the tube and the blood therein;
   means for detecting light from said light transmitting means after the light has been transmitted through the blood in the tube, and for producing signals representative of changes in optical density of the light so detected at a controlled flow rate of the blood and when the flow of blood is stopped by said bringing said piston to said full stop;
   means for receiving said signals to determine, the aggregation rate of the red blood cells; and
   a spring biasing said piston in an opposite direction, said solenoid moving said piston in said one direction and said spring returning said piston in said opposite direction.

6. The apparatus of claim 5, wherein said syringe is disposed horizontally above said solenoid, and said spring is connected to said plunger.